United States Patent [19]

Barr et al.

[11] Patent Number: 5,460,950
[45] Date of Patent: Oct. 24, 1995

[54] EXPRESSION OF PACE IN HOST CELLS AND METHODS OF USE THEREOF

[75] Inventors: Philip J. Barr; Anthony J. Brake, both of Berkeley, Calif.; Randal J. Kaufman, Boston; Louise Wasley, Medfield, both of Mass.; Patricia Tekamp-Olson, San Anselmo; Polly A. Wong, Mountain View, both of Calif.

[73] Assignees: Genetics Institute, Inc., Cambridge, Mass.; Chiron Corporation, Emeryville, Calif.

[21] Appl. No.: 885,972

[22] Filed: May 20, 1992

Related U.S. Application Data

[63] Continuation-in-part of Ser. No. 621,092, Nov. 26, 1990, abandoned, and a continuation-in-part of Ser. No. 620,859, Nov. 29, 1990, abandoned, and a continuation-in-part of Ser. No. 621,443, Nov. 29, 1990, abandoned, and a continuation-in-part of Ser. No. 621,457, Nov. 30, 1990, abandoned.

[51] Int. Cl.$^6$ .......................... G12N 15/00; G12N 15/57; G12N 15/81; G12N 15/85
[52] U.S. Cl. .................. 435/69.1; 435/69.6; 435/219; 435/226; 435/252.3; 435/320.1; 935/28; 935/32; 935/69; 935/70; 935/71; 935/60
[58] Field of Search ............................ 435/69.1, 219, 435/226, 252.3, 320.1; 536/23.2

[56] References Cited

U.S. PATENT DOCUMENTS

| | | | |
|---|---|---|---|
| 4,652,639 | 3/1987 | Stabinsky | 536/271 |
| 4,745,051 | 5/1988 | Smith et al. | 435/69.1 |
| 4,770,999 | 9/1988 | Kaufman et al. | 435/68 |
| 4,784,950 | 11/1988 | Hagen et al. | 435/68 |
| 4,870,023 | 9/1989 | Fraser et al. | 435/320.1 |
| 4,929,553 | 5/1990 | Bussey et al. | 435/172.3 |
| 4,992,373 | 2/1991 | Bang et al. | 435/226 |
| 5,004,803 | 4/1991 | Kaufman et al. | 530/383 |
| 5,041,378 | 8/1991 | Drummond et al. | 435/234 |
| 5,059,528 | 10/1991 | Bollen et al. | 435/69.4 |
| 5,077,204 | 12/1991 | Brake et al. | 435/681 |

FOREIGN PATENT DOCUMENTS

| | | |
|---|---|---|
| 246709 | 11/1987 | European Pat. Off. . |
| WO91/06314 | 5/1991 | WIPO . |
| US91/08725 | 11/1991 | WIPO . |

OTHER PUBLICATIONS

Fontkamp, E., et al., 1986, DNA, 5(6):511–517.
Schalloen, J. A., et al., 1987, Journal of Clinical Investigation, 80:1545–1549.
D. C. Foster et al, Thrombosis and Haemostasis, 62:321 (1989).
C. K. Derian et al, J. Biol. Chem., 264(12):6615–6618 (1989).
R. J. Kaufman et al, J. Biol. Chem., 261(21):9622–9628 (1986).
A. M. W. van den Ouwelan et al, Nucl. Acids. Res., 18(3):664 (1990).
S. P. Smeekens et al, J. Biol. Chem., 265(6):2997–3000 (1990).
B. Furie et al, Cell, 53:505–518 (1988).
G. Thomas et al, Science, 241:226–230 (1988).
I. M. Dickerson et al, J. Biol. Chem., 265:2462 (1990).
T. Achstetter et al, EMBO J. 4:173 (1985).
K. Mizuno et al, Biochem. Biophys. Res. Commun., 144:807 (1987).
D. Julius et al, Cell, 37:1075 (1984).
D. Julius et al, Cell, 36:309 (1984).
A. J. M. Roebroek et al, EMBO J., 5:2197 (1986).
E. A. Wang et al, Proc. Natl. Acad. Sci. USA, 87:2220–2224 (1990).
R. S. Fuller et al, Proc. Natl. Acad. Sci. USA, 86:1434–1438 (1989).
I. C. Bathurst et al, Science, 235:348–350 (1987).
R. S. Fuller et al, Science, 246:482–486 (1989).
A. J. M. Roebroek et al, Molec. Biol. Rep., 11:117–125 (1986).
R. S. Fuller et al, Microbiology, 1986:273–278 (1986).
R. J. Wise et al, Proc. Natl. Acad. Sci. USA, 87:9378–9382 (1990).
R. J. Wise et al, "Expression of a Human Proprotein Processing Enzyme that Correctly Cleaves the Von Willebrand Factor Precursor at its Dibasis Amino Acid Recognition Site," The International Society of Hematology 23rd Congress the American Society of Hematology 32nd Annual Meeting (Abstract of talk at meeting 1990).
R. J. Kaufman et al, "Rate Limiting Steps in the Syntheses and Secretion of Heterologous Proteins in Mammalian Cells," The Proceedings of the Fifth European Congress of Biotechnology, Eds. Christiansen, Munck, Villadsen, Vol. 2, Munksgaard Int. Publ. Copenhagen pp. 715–719 (1990).
N. G. Seidah et al, DNA and Cell Biology, 9(6):415–424 (1990).
Y. Misumi et al, Nucleic Acid Res., 18(22):6719 (1990).
M. W. Pantoliano et al, Biochem., 26:2077–2082 (1987).
A. J. Russell et al, J. Mol. Biol., 193:803–813 (1987).
J. A. Wells et al, Proc. Natl. Acad. Sci. USA, 84:1219–1223 (1987).
Y. Ikehara et al, "Functional Expression of Furin Demonstrating its Intracellular Localization and Proprotein–Processing Activity", Abstract No. 3SC–1630, *Cell Struct. Function*, 16:541 (1991).
K. Hatsuzawa et al, "Structure and Expression of Mouse Furin, a Yeast Kex2-related Protease", *J. Biol. Chem.*, 265(36): 22075–22078 (Dec. 25, 1990).

(List continued on next page.)

*Primary Examiner*—Robert A. Wax
*Assistant Examiner*—William W. Moore
*Attorney, Agent, or Firm*—Howson and Howson

[57] ABSTRACT

Compositions and methods are provided for endopeptidase production and for enhanced efficiencies of processing heterologous precursor polypeptides to mature polypeptides, including proteins requiring gamma-carboxylation for biological activity. These compositions and methods utilize recombinant PACE, a mammalian endopeptidase that is specific for dibasic amino acid sites.

60 Claims, 12 Drawing Sheets

OTHER PUBLICATIONS

Y. Misumi et al, "Functional Expression of Furin Demonstrating its Intracellular Localization and Endoprotease Activity for Processing of Proalbumin and Complement Pre–C3", *J. Biol. Chem.*, 266(25): 16954–16959 (Sept. 5, 1991).

A Rehemtulla et al, "Preferred Sequence Requirements for Cleavage of Pro–von Willebrand Factor by Propeptide–Processing Enzymes", *Blood*, 79(9):2349–2355 (May 1, 1992).

Kiefer, M. C., et al, 1991, DNA and Cell Biology, 10(10):757–769.

Kaufman, R. J. et al., 1987 The EMBO Journal, 6(1):187–193.

Kaufman, R. J., et al. Mar. 1989, Molecular and Cellular Biology, 9(3):946–958.

Ehrlich, H. J. et al, Aug. 1958, The Journal of Biological Chemistry, 264(24):14298–14304.

Van den Ouweland, A. M. W. et al., Sep. 1989, Nuebeic Acids Research, 17(17):7101–7102.

Van de Ven, W. J. M., et al., Dec. 1990, Molecular Biology Reports, 14:265–275.

Kaufman, R. J., 1990, Methods in Enzymology, 185:537–566.

Breshahan, P. A., et al., 1990, The Journal of Cell Biology, III(6):2851–2859.

Kaufman, T. J., et al., 1991, Neubeic Acids Research, 19(16):4485–4490.

Roebroek, A. J. M., et al., 1991, FEBS Letters, 289(2):133–137.

Van de ven, W. J. M., et al., 1992, Enzyme, 45(5):257–270.

Rehemtalla, A., et al., 1992, Proceedings of the National Academy of Sciences, USA, 89:8235–8239.

Wasley, L. C., et al., 1993, The Journal of Biological Chemistry, 268(12):8458–8465.

Fig. 1A

| | |
|---|---|
| ATG GAG CTG AGG CCC TGG TTG CTA TGG GTG GTA GCA GCA<br>Met Glu Leu Arg Pro Trp Leu Leu Trp Val Val Ala Ala<br>1                  5                        10 | 39 |
| ACA GGA ACC TTG GTC CTG CTA GCA GCT GAT GCT CAG GGC<br>Thr Gly Thr Leu Val Leu Leu Ala Ala Asp Ala Gln Gly<br>      15                     20                       25 | 78 |
| CAG AAG GTC TTC ACC AAC ACG TGG GCT GTG CGC ATC CCT<br>Gln Lys Val Phe Thr Asn Thr Trp Ala Val Arg Ile Pro<br>              30                        35 | 117 |
| GGA GGC CCA GCG GTG GCC AAC AGT GTG GCA CGG AAG CAT<br>Gly Gly Pro Ala Val Ala Asn Ser Val Ala Arg Lys His<br>40                        45                     50 | 156 |
| GGG TTC CTC AAC CTG GGC CAG ATC TTC GGG GAC TAT TAC<br>Gly Phe Leu Asn Leu Gly Gln Ile Phe Gly Asp Tyr Tyr<br>          55                       60                  65 | 195 |
| CAC TTC TGG CAT CGA GGA GTG ACG AAG CGG TCC CTG TCG<br>His Phe Trp His Arg Gly Val Thr Lys Arg Ser Leu Ser<br>                  70                           75 | 234 |
| CCT CAC CGC CCG CGG CAC AGC CGG CTG CAG AGG GAG CCT<br>Pro His Arg Pro Arg His Ser Arg Leu Gln Arg Glu Pro<br>      80                     85                     90 | 273 |
| CAA GTA CAG TGG CTG GAA CAG CAG GTG GCA AAG CGA CGG<br>Gln Val Gln Trp Leu Glu Gln Gln Val Ala Lys Arg Arg<br>              95                       100 | 312 |
| ACT AAA CGG GAC GTG TAC CAG GAG CCC ACA GAC CCC AAG<br>Thr Lys Arg Asp Val Tyr Gln Glu Pro Thr Asp Pro Lys<br>105                   110                     115 | 351 |
| TTT CCT CAG CAG TGG TAC CTG TCT GGT GTC ACT CAG CGG<br>Phe Pro Gln Gln Trp Tyr Leu Ser Gly Val Thr Gln Arg<br>        120                     125                130 | 390 |
| GAC CTG AAT GTG AAG GCG GCC TGG GCG CAG GGC TAC ACA<br>Asp Leu Asn Val Lys Ala Ala Trp Ala Gln Gly Tyr Thr<br>               135                     140 | 429 |
| GGG CAC GGC ATT GTG GTC TCC ATT CTG GAC GAT GGC ATC<br>Gly His Gly Ile Val Val Ser Ile Leu Asp Asp Gly Ile<br>145                   150                     155 | 468 |

Fig. 1B

| | | | | | | | | | | | | |
|---|---|---|---|---|---|---|---|---|---|---|---|---|
| GAG | AAG | AAC | CAC | CCG | GAC | TTG | GCA | GGC | AAT | TAT | GAT | CCT | 507 |
| Glu | Lys | Asn | His | Pro | Asp | Leu | Ala | Gly | Asn | Tyr | Asp | Pro | |
| | | | 160 | | | | | 165 | | | | | |

```
GAG AAG AAC CAC CCG GAC TTG GCA GGC AAT TAT GAT CCT     507
Glu Lys Asn His Pro Asp Leu Ala Gly Asn Tyr Asp Pro
            160                 165

GGG GCC AGT TTT GAT GTC AAT GAC CAG GAC CCT GAC CCC     546
Gly Ala Ser Phe Asp Val Asn Asp Gln Asp Pro Asp Pro
170                 175                 180

CAG CCT CGG TAC ACA CAG ATG AAT GAC AAC AGG CAC GGC     585
Gln Pro Arg Tyr Thr Gln Met Asn Asp Asn Arg His Gly
        185                 190                 195

ACA CGG TGT GCG GGG GAA GTG GCT GCG GTG GCC AAC AAC     624
Thr Arg Cys Ala Gly Glu Val Ala Ala Val Ala Asn Asn
                200                 205

GGT GTC TGT GGT GTA GGT GTG GCC TAC AAC GCC CGC ATT     663
Gly Val Cys Gly Val Gly Val Ala Tyr Asn Ala Arg Ile
        210                 215                 220

GGA GGG GTG CGC ATG CTG GAT GGC GAG GTG ACA GAT GCA     702
Gly Gly Val Arg Met Leu Asp Gly Glu Val Thr Asp Ala
                225                 230

GTG GAG GCA CGC TCG CTG GGC CTG AAC CCC AAC CAC ATC     741
Val Glu Ala Arg Ser Leu Gly Leu Asn Pro Asn His Ile
235                 240                 245

CAC ATC TAC AGT GCC AGC TGG GGC CCC GAG GAT GAC GGC     780
His Ile Tyr Ser Ala Ser Trp Gly Pro Glu Asp Asp Gly
        250                 255                 260

AAG ACA GTG GAT GGG CCA GCC CGC CTC GCC GAG GAG GCC     819
Lys Thr Val Asp Gly Pro Ala Arg Leu Ala Glu Glu Ala
                265                 270

TTC TTC CGT GGG GTT AGC CAG GGC CGA GGG GGG CTG GGC     858
Phe Phe Arg Gly Val Ser Gln Gly Arg Gly Gly Leu Gly
275                 280                 285

TCC ATC TTT GTC TGG GCC TCG GGG AAC GGG GGC CGG GAA     897
Ser Ile Phe Val Trp Ala Ser Gly Asn Gly Gly Arg Glu
        290                 295

CAT GAC AGC TGC AAC TGC GAC GGC TAC ACC AAC AGT ATC     936
His Asp Ser Cys Asn Cys Asp Gly Tyr Thr Asn Ser Ile
300                 305                 310
```

Fig. 1C

| | | | | | | | | | | | |
|---|---|---|---|---|---|---|---|---|---|---|---|
| TAC | ACG | CTG | TCC | ATC | AGC | AGC | GCC | ACG | CAG | TTT | GGC | AAC | 975 |
| Tyr | Thr | Leu | Ser | Ile | Ser | Ser | Ala | Thr | Gln | Phe | Gly | Asn |
| | | 315 | | | | 320 | | | | | | 325 |

```
TAC ACG CTG TCC ATC AGC AGC GCC ACG CAG TTT GGC AAC        975
Tyr Thr Leu Ser Ile Ser Ser Ala Thr Gln Phe Gly Asn
        315             320                     325

GTG CCG TGG TAC AGC GAG GCC TGC TCG TCC ACA CTG GCC        1014
Val Pro Trp Tyr Ser Glu Ala Cys Ser Ser Thr Leu Ala
                330             335

ACG ACC TAC AGC AGT GGC AAC CAG AAT GAG AAG CAG ATC        1053
Thr Thr Tyr Ser Ser Gly Asn Gln Asn Glu Lys Gln Ile
    340             345             350

GTG ACG ACT GAC TTG CGG CAG AAG TGC ACG GAG TCT CAC        1092
Val Thr Thr Asp Leu Arg Gln Lys Cys Thr Glu Ser His
            355             360

ACG GGC ACC TCA GCC TCT GCC CCC TTA GCA GCC GGC ATC        1131
Thr Gly Thr Ser Ala Ser Ala Pro Leu Ala Ala Gly Ile
365             370             375

ATT GCT CTC ACC CTG GAG GCC AAT AAG AAC CTC ACA TGG        1170
Ile Ala Leu Thr Leu Glu Ala Asn Lys Asn Leu Thr Trp
        380             385             390

CGG GAC ATG CAA CAC CTG GTG GTA CAG ACC TCG AAG CCA        1209
Arg Asp Met Gln His Leu Val Val Gln Thr Ser Lys Pro
                395             400

GCC CAC CTC AAT GCC AAC GAC TGG GCC ACC AAT GGT GTG        1248
Ala His Leu Asn Ala Asn Asp Trp Ala Thr Asn Gly Val
    405             410             415

GGG CGG AAA GTG AGC CAC TCA TAT GGC TAC GGG CTT TTG        1287
Gly Arg Lys Val Ser His Ser Tyr Gly Tyr Gly Leu Leu
            420             425

GAC GCA GGC GCC ATG GTG GCC CTG GCC CAG AAT TGG ACC        1326
Asp Ala Gly Ala Met Val Ala Leu Ala Gln Asn Trp Thr
430             435             440

ACA GTG GCC CCC CAG CGG AAG TGC ATC ATC GAC ATC CTC        1365
Thr Val Ala Pro Gln Arg Lys Cys Ile Ile Asp Ile Leu
        445             450             455

ACC GAG CCC AAA GAC ATC GGG AAA CGG CTC GAG GTG CGG        1404
Thr Glu Pro Lys Asp Ile Gly Lys Arg Leu Glu Val Arg
                460             465
```

Fig. 1D

| | | | | | | | | | | | |
|---|---|---|---|---|---|---|---|---|---|---|---|
| AAG | ACC | GTG | ACC | GCG | TGC | CTG | GGC | GAG | CCC | AAC | CAC ATC | 1443
| Lys | Thr | Val | Thr | Ala | Cys | Leu | Gly | Glu | Pro | Asn | His Ile |
| | 470 | | | | 475 | | | | | 480 | |

ACT CGG CTG GAG CAC GCT CAG GCG CGG CTC ACC CTG TCC   1482
Thr Arg Leu Glu His Ala Gln Ala Arg Leu Thr Leu Ser
            485             490

TAT AAT CGC CGT GGC GAC CTG GCC ATC CAC CTG GTC AGC   1521
Tyr Asn Arg Arg Gly Asp Leu Ala Ile His Leu Val Ser
495           500           505

CCC ATG GGC ACC CGC TCC ACC CTG CTG GCA GCC AGG CCA   1560
Pro Met Gly Thr Arg Ser Thr Leu Leu Ala Ala Arg Pro
        510           515           520

CAT GAC TAC TCC GCA GAT GGG TTT AAT GAC TGG GCC TTC   1599
His Asp Tyr Ser Ala Asp Gly Phe Asn Asp Trp Ala Phe
                525           530

ATG ACA ACT CAT TCC TGG GAT GAG GAT CCC TCT GGC GAG   1638
Met Thr Thr His Ser Trp Asp Glu Asp Pro Ser Gly Glu
535           540           545

TGG GTC CTA GAG ATT GAA AAC ACC AGC GAA GCC AAC AAC   1677
Trp Val Leu Glu Ile Glu Asn Thr Ser Glu Ala Asn Asn
            550           555

TAT GGG ACG CTG ACC AAG TTC ACC CTC GTA CTC TAT GGC   1716
Tyr Gly Thr Leu Thr Lys Phe Thr Leu Val Leu Tyr Gly
560           565           570

ACC GCC CCT GAG GGG CTG CCC GTA CCT CCA GAA AGC AGT   1755
Thr Ala Pro Glu Gly Leu Pro Val Pro Pro Glu Ser Ser
        575           580           585

GGC TGC AAG ACC CTC ACG TCC AGT CAG GCC TGT GTG GTG   1794
Gly Cys Lys Thr Leu Thr Ser Ser Gln Ala Cys Val Val
            590           595

TGC GAG GAA GGC TTC TCC CTG CAC CAG AAG AGC TGT GTC   1833
Cys Glu Glu Gly Phe Ser Leu His Gln Lys Ser Cys Val
    600           605           610

CAG CAC TGC CCT CCA GGC TTC GCC CCC CAA GTC CTC GAT   1872
Gln His Cys Pro Pro Gly Phe Ala Pro Gln Val Leu Asp
            615           620

Fig. 1E

| | | | | | | | | | | | |
|---|---|---|---|---|---|---|---|---|---|---|---|
| ACG | CAC | TAT | AGC | ACC | GAG | AAT | GAC | GTG | GAG | ACC | ATC CGG | 1911 |
| Thr | His | Tyr | Ser | Thr | Glu | Asn | Asp | Val | Glu | Thr | Ile Arg |
| 625 | | | | | 630 | | | | | 635 | |

```
ACG CAC TAT AGC ACC GAG AAT GAC GTG GAG ACC ATC CGG    1911
Thr His Tyr Ser Thr Glu Asn Asp Val Glu Thr Ile Arg
625                 630                 635

GCC AGC GTC TGC GCC CCC TGC CAC GCC TCA TGT GCC ACA    1950
Ala Ser Val Cys Ala Pro Cys His Ala Ser Cys Ala Thr
        640                 645                 650

TGC CAG GGG CCG GCC CTG ACA GAC TGC CTC AGC TGC CCC    1989
Cys Gln Gly Pro Ala Leu Thr Asp Cys Leu Ser Cys Pro
                655                 660

AGC CAC GCC TCC TTG GAC CCT GTG GAG CAG ACT TGC TCC    2028
Ser His Ala Ser Leu Asp Pro Val Glu Gln Thr Cys Ser
665                 670                 675

CGG CAA AGC CAG AGC AGC CGA GAG TCC CCG CCA CAG CAG    2067
Arg Gln Ser Gln Ser Ser Arg Glu Ser Pro Pro Gln Gln
        680                 685

CAG CCA CCT CGG CTG CCC CCG GAG GTG GAG GCG GGG CAA    2106
Gln Pro Pro Arg Leu Pro Pro Glu Val Glu Ala Gly Gln
690                 695                 700

CGG CTG CGG GCA GGG CTG CTG CCC TCA CAC CTG CCT GAG    2145
Arg Leu Arg Ala Gly Leu Leu Pro Ser His Leu Pro Glu
            705                 710                 715

GTG GTG GCC GGC CTC AGC TGC GCC TTC ATC GTG CTG GTC    2184
Val Val Ala Gly Leu Ser Cys Ala Phe Ile Val Leu Val
                720                 725

TTC GTC ACT GTC TTC CTG GTC CTG CAG CTG CGC TCT GGC    2223
Phe Val Thr Val Phe Leu Val Leu Gln Leu Arg Ser Gly
        730                 735                 740

TTT AGT TTT CGG GGG GTG AAG GTG TAC ACC ATG GAC CGT    2262
Phe Ser Phe Arg Gly Val Lys Val Tyr Thr Met Asp Arg
                745                 750

GGC CTC ATC TCC TAC AAG GGG CTG CCC CCT GAA GCC TGG    2301
Gly Leu Ile Ser Tyr Lys Gly Leu Pro Pro Glu Ala Trp
755                 760                 765

CAG GAG GAG TGC CCG TCT GAC TCA GAA GAG GAC GAG GGC    2340
Gln Glu Glu Cys Pro Ser Asp Ser Glu Glu Asp Glu Gly
            770                 775                 780
```

Fig. 1F

```
CGG GGC GAG AGG ACC GCC TTT ATC AAA GAC CAG AGC GCC   2379
Arg Gly Glu Arg Thr Ala Phe Ile Lys Asp Gln Ser Ala
                785                 790

CTC TGA                                                2385
Leu End
    795
```

Fig. 2A

```
                                              GAATTCG   -401
GAGATCTACA GGGCTGCCCC CGCCCGCGCC GGAGCTGGAG CCCAGGCCGA  -351
GCCCTGCCCT GGTCGCCGGC CGGGCCGAGG CCGCGCCGCC GCGCCTCCCC  -301
GCCTCCGCGC CGTGACGCTG CCGCCGGGCG CGGGGACCGC GCCGAGCCCA  -251
GGCCCCCGCC GCCGGGCTCT CCGCTCGGCC GAGGGGCGCC CGAGCCGCCG  -201
CGGCGGTCGC CTGGAAAAGT TTCCCCGCCA GGGCTCCCCA GGGGTCGGCA  -151
CTCTTCACCC TCCCGAGCCC TGCCCGTCTC GGCCCCATGC CCCCACCAGT  -101
CAGCCCCGGG CCACAGGCAG TGAGCAGGCA CCTGGGAGCC GAGGCCTGTG  - 51
ACCAGGCCAA GGAGACGGGC GCTCCAGGGT CCCAGCCACC TGTCCCCCCC  -  1
```

| | | | | | | | | | | |
|---|---|---|---|---|---|---|---|---|---|---|
| ATG | GAG | CTG | AGG | CCC | TGG | TTG | CTA | TGG | GTG GTA GCA GCA | 39 |
| Met | Glu | Leu | Arg | Pro | Trp | Leu | Leu | Trp | Val Val Ala Ala | |
| 1 | | | | 5 | | | | | 10 | |

| ACA | GGA | ACC | TTG | GTC | CTG | CTA | GCA | GCT | GAT GCT CAG GGC | 78 |
|---|---|---|---|---|---|---|---|---|---|---|
| Thr | Gly | Thr | Leu | Val | Leu | Leu | Ala | Ala | Asp Ala Gln Gly | |
| | | 15 | | | | 20 | | | 25 | |

| CAG | AAG | GTC | TTC | ACC | AAC | ACG | TGG | GCT | GTG CGC ATC CCT | 117 |
|---|---|---|---|---|---|---|---|---|---|---|
| Gln | Lys | Val | Phe | Thr | Asn | Thr | Trp | Ala | Val Arg Ile Pro | |
| | | | 30 | | | | 35 | | | |

| GGA | GGC | CCA | GCG | GTG | GCC | AAC | AGT | GTG | GCA CGG AAG CAT | 156 |
|---|---|---|---|---|---|---|---|---|---|---|
| Gly | Gly | Pro | Ala | Val | Ala | Asn | Ser | Val | Ala Arg Lys His | |
| 40 | | | | 45 | | | | 50 | | |

| GGG | TTC | CTC | AAC | CTG | GGC | CAG | ATC | TTC | GGG GAC TAT TAC | 195 |
|---|---|---|---|---|---|---|---|---|---|---|
| Gly | Phe | Leu | Asn | Leu | Gly | Gln | Ile | Phe | Gly Asp Tyr Tyr | |
| | | 55 | | | | 60 | | | 65 | |

| CAC | TTC | TGG | CAT | CGA | GGA | GTG | ACG | AAG | CGG TCC CTG TCG | 234 |
|---|---|---|---|---|---|---|---|---|---|---|
| His | Phe | Trp | His | Arg | Gly | Val | Thr | Lys | Arg Ser Leu Ser | |
| | | | 70 | | | | 75 | | | |

| CCT | CAC | CGC | CCG | CGG | CAC | AGC | CGG | CTG | CAG AGG GAG CCT | 273 |
|---|---|---|---|---|---|---|---|---|---|---|
| Pro | His | Arg | Pro | Arg | His | Ser | Arg | Leu | Gln Arg Glu Pro | |
| | 80 | | | | 85 | | | | 90 | |

| CAA | GTA | CAG | TGG | CTG | GAA | CAG | CAG | GTG | GCA AAG CGA CGG | 312 |
|---|---|---|---|---|---|---|---|---|---|---|
| Gln | Val | Gln | Trp | Leu | Glu | Gln | Gln | Val | Ala Lys Arg Arg | |
| | | | 95 | | | | 100 | | | |

| ACT | AAA | CGG | GAC | GTG | TAC | CAG | GAG | CCC | ACA GAC CCC AAG | 351 |
|---|---|---|---|---|---|---|---|---|---|---|
| Thr | Lys | Arg | Asp | Val | Tyr | Gln | Glu | Pro | Thr Asp Pro Lys | |
| 105 | | | | 110 | | | | 115 | | |

| TTT | CCT | CAG | CAG | TGG | TAC | CTG | TCT | GGT | GTC ACT CAG CGG | 390 |
|---|---|---|---|---|---|---|---|---|---|---|
| Phe | Pro | Gln | Gln | Trp | Tyr | Leu | Ser | Gly | Val Thr Gln Arg | |
| | | 120 | | | | 125 | | | 130 | |

Fig. 2B

| | | | | | | | | | | | | |
|---|---|---|---|---|---|---|---|---|---|---|---|---|
| GAC | CTG | AAT | GTG | AAG | GCG | GCC | TGG | GCG | CAG | GGC | TAC | ACA | 429
| Asp | Leu | Asn | Val | Lys | Ala | Ala | Trp | Ala | Gln | Gly | Tyr | Thr |
| | | | 135 | | | | | 140 | | | | |
| GGG | CAC | GGC | ATT | GTG | GTC | TCC | ATT | CTG | GAC | GAT | GGC | ATC | 468
| Gly | His | Gly | Ile | Val | Val | Ser | Ile | Leu | Asp | Asp | Gly | Ile |
| | 145 | | | | 150 | | | | | 155 | | |
| GAG | AAG | AAC | CAC | CCG | GAC | TTG | GCA | GGC | AAT | TAT | GAT | CCT | 507
| Glu | Lys | Asn | His | Pro | Asp | Leu | Ala | Gly | Asn | Tyr | Asp | Pro |
| | | | 160 | | | | | 165 | | | | |
| GGG | GCC | AGT | TTT | GAT | GTC | AAT | GAC | CAG | GAC | CCT | GAC | CCC | 546
| Gly | Ala | Ser | Phe | Asp | Val | Asn | Asp | Gln | Asp | Pro | Asp | Pro |
| 170 | | | | 175 | | | | | 180 | | | |
| CAG | CCT | CGG | TAC | ACA | CAG | ATG | AAT | GAC | AAC | AGG | CAC | GGC | 585
| Gln | Pro | Arg | Tyr | Thr | Gln | Met | Asn | Asp | Asn | Arg | His | Gly |
| | | 185 | | | | | 190 | | | | | 195 |
| ACA | CGG | TGT | GCG | GGG | GAA | GTG | GCT | GCG | GTG | GCC | AAC | AAC | 624
| Thr | Arg | Cys | Ala | Gly | Glu | Val | Ala | Ala | Val | Ala | Asn | Asn |
| | | | | 200 | | | | | 205 | | | |
| GGT | GTC | TGT | GGT | GTA | GGT | GTG | GCC | TAC | AAC | GCC | CGC | ATT | 663
| Gly | Val | Cys | Gly | Val | Gly | Val | Ala | Tyr | Asn | Ala | Arg | Ile |
| | 210 | | | | | 215 | | | | | 220 | |
| GGA | GGG | GTG | CGC | ATG | CTG | GAT | GGC | GAG | GTG | ACA | GAT | GCA | 702
| Gly | Gly | Val | Arg | Met | Leu | Asp | Gly | Glu | Val | Thr | Asp | Ala |
| | | | 225 | | | | | 230 | | | | |
| GTG | GAG | GCA | CGC | TCG | CTG | GGC | CTG | AAC | CCC | AAC | CAC | ATC | 741
| Val | Glu | Ala | Arg | Ser | Leu | Gly | Leu | Asn | Pro | Asn | His | Ile |
| 235 | | | | | 240 | | | | | 245 | | |
| CAC | ATC | TAC | AGT | GCC | AGC | TGG | GGC | CCC | GAG | GAT | GAC | GGC | 780
| His | Ile | Tyr | Ser | Ala | Ser | Trp | Gly | Pro | Glu | Asp | Asp | Gly |
| | | 250 | | | | | 255 | | | | | 260 |
| AAG | ACA | GTG | GAT | GGG | CCA | GCC | CGC | CTC | GCC | GAG | GAG | GCC | 819
| Lys | Thr | Val | Asp | Gly | Pro | Ala | Arg | Leu | Ala | Glu | Glu | Ala |
| | | | | 265 | | | | | 270 | | | |
| TTC | TTC | CGT | GGG | GTT | AGC | CAG | GGC | CGA | GGG | GGG | CTG | GGC | 858
| Phe | Phe | Arg | Gly | Val | Ser | Gln | Gly | Arg | Gly | Gly | Leu | Gly |
| | | 275 | | | | | 280 | | | | | 285 |
| TCC | ATC | TTT | GTC | TGG | GCC | TCG | GGG | AAC | GGG | GGC | CGG | GAA | 897
| Ser | Ile | Phe | Val | Trp | Ala | Ser | Gly | Asn | Gly | Gly | Arg | Glu |
| | | | | 290 | | | | | 295 | | | |

Fig. 2C

```
CAT GAC AGC TGC AAC TGC GAC GGC TAC ACC AAC AGT ATC         936
His Asp Ser Cys Asn Cys Asp Gly Tyr Thr Asn Ser Ile
300                 305                 310

TAC ACG CTG TCC ATC AGC AGC GCC ACG CAG TTT GGC AAC         975
Tyr Thr Leu Ser Ile Ser Ser Ala Thr Gln Phe Gly Asn
        315                 320                 325

GTG CCG TGG TAC AGC GAG GCC TGC TCG TCC ACA CTG GCC        1014
Val Pro Trp Tyr Ser Glu Ala Cys Ser Ser Thr Leu Ala
                330                 335

ACG ACC TAC AGC AGT GGC AAC CAG AAT GAG AAG CAG ATC        1053
Thr Thr Tyr Ser Ser Gly Asn Gln Asn Glu Lys Gln Ile
340                 345                 350

GTG ACG ACT GAC TTG CGG CAG AAG TGC ACG GAG TCT CAC        1092
Val Thr Thr Asp Leu Arg Gln Lys Cys Thr Glu Ser His
        355                 360

ACG GGC ACC TCA GCC TCT GCC CCC TTA GCA GCC GGC ATC        1131
Thr Gly Thr Ser Ala Ser Ala Pro Leu Ala Ala Gly Ile
365                 370                 375

ATT GCT CTC ACC CTG GAG GCC AAT AAG AAC CTC ACA TGG        1170
Ile Ala Leu Thr Leu Glu Ala Asn Lys Asn Leu Thr Trp
        380                 385                 390

CGG GAC ATG CAA CAC CTG GTG GTA CAG ACC TCG AAG CCA        1209
Arg Asp Met Gln His Leu Val Val Gln Thr Ser Lys Pro
                395                 400

GCC CAC CTC AAT GCC AAC GAC TGG GCC ACC AAT GGT GTG        1248
Ala His Leu Asn Ala Asn Asp Trp Ala Thr Asn Gly Val
        405                 410                 415

GGC CGG AAA GTG AGC CAC TCA TAT GGC TAC GGG CTT TTG        1287
Gly Arg Lys Val Ser His Ser Tyr Gly Tyr Gly Leu Leu
                420                 425

GAC GCA GGC GCC ATG GTG GCC CTG GCC CAG AAT TGG ACC        1326
Asp Ala Gly Ala Met Val Ala Leu Ala Gln Asn Trp Thr
430                 435                 440

ACA GTG GCC CCC CAG CGG AAG TGC ATC ATC GAC ATC CTC        1365
Thr Val Ala Pro Gln Arg Lys Cys Ile Ile Asp Ile Leu
        445                 450                 455

ACC GAG CCC AAA GAC ATC GGG AAA CGG CTC GAG GTG CGG        1404
Thr Glu Pro Lys Asp Ile Gly Lys Arg Leu Glu Val Arg
                460                 465
```

Fig. 2D

| | |
|---|---|
| AAG ACC GTG ACC GCG TGC CTG GGC GAG CCC AAC CAC ATC<br>Lys Thr Val Thr Ala Cys Leu Gly Glu Pro Asn His Ile<br>470                            475                       480 | 1443 |
| ACT CGG CTG GAG CAC GCT CAG GCG CGG CTC ACC CTG TCC<br>Thr Arg Leu Glu His Ala Gln Ala Arg Leu Thr Leu Ser<br>                485                       490 | 1482 |
| TAT AAT CGC CGT GGC GAC CTG GCC ATC CAC CTG GTC AGC<br>Tyr Asn Arg Arg Gly Asp Leu Ala Ile His Leu Val Ser<br>495                       500                   505 | 1521 |
| CCC ATG GGC ACC CGC TCC ACC CTG CTG GCA GCC AGG CCA<br>Pro Met Gly Thr Arg Ser Thr Leu Leu Ala Ala Arg Pro<br>         510                   515             520 | 1560 |
| CAT GAC TAC TCC GCA GAT GGG TTT AAT GAC TGG GCC TTC<br>His Asp Tyr Ser Ala Asp Gly Phe Asn Asp Trp Ala Phe<br>                525                   530 | 1599 |
| ATG ACA ACT CAT TCC TGG GAT GAG GAT CCC TCT GGC GAG<br>Met Thr Thr His Ser Trp Asp Glu Asp Pro Ser Gly Glu<br>535                       540                   545 | 1638 |
| TGG GTC CTA GAG ATT GAA AAC ACC AGC GAA GCC AAC AAC<br>Trp Val Leu Glu Ile Glu Asn Thr Ser Glu Ala Asn Asn<br>            550                   555 | 1677 |
| TAT GGG ACG CTG ACC AAG TTC ACC CTC GTA CTC TAT GGC<br>Tyr Gly Thr Leu Thr Lys Phe Thr Leu Val Leu Tyr Gly<br>560                         565                 570 | 1716 |
| ACC GCC CCT GAG GGG CTG CCC GTA CCT CCA GAA AGC AGT<br>Thr Ala Pro Glu Gly Leu Pro Val Pro Pro Glu Ser Ser<br>         575                   580             585 | 1755 |
| GGC TGC AAG ACC CTC ACG TCC AGT CAG GCC TGT GTG GTG<br>Gly Cys Lys Thr Leu Thr Ser Ser Gln Ala Cys Val Val<br>                590                   595 | 1794 |
| TGC GAG GAA GGC TTC TCC CTG CAC CAG AAG AGC TGT GTC<br>Cys Glu Glu Gly Phe Ser Leu His Gln Lys Ser Cys Val<br>600                       605                 610 | 1833 |
| CAG CAC TGC CCT CCA GGC TTC GCC CCC CAA GTC CTC GAT<br>Gln His Cys Pro Pro Gly Phe Ala Pro Gln Val Leu Asp<br>         615                   620 | 1872 |
| ACG CAC TAT AGC ACC GAG AAT GAC GTG GAG ACC ATC CGG<br>Thr His Tyr Ser Thr Glu Asn Asp Val Glu Thr Ile Arg<br>625                       630                   635 | 1911 |

Fig. 2E

| | | | | | | | | | | | | |
|---|---|---|---|---|---|---|---|---|---|---|---|---|
| GCC | AGC | GTC | TGC | GCC | CCC | TGC | CAC | GCC | TCA | TGT | GCC | ACA | 1950 |
| Ala | Ser | Val | Cys | Ala | Pro | Cys | His | Ala | Ser | Cys | Ala | Thr | |
| | | 640 | | | | 645 | | | | | | 650 | |

```
GCC AGC GTC TGC GCC CCC TGC CAC GCC TCA TGT GCC ACA      1950
Ala Ser Val Cys Ala Pro Cys His Ala Ser Cys Ala Thr
        640             645                     650

TGC CAG GGG CCG GCC CTG ACA GAC TGC CTC AGC TGC CCC      1989
Cys Gln Gly Pro Ala Leu Thr Asp Cys Leu Ser Cys Pro
                655             660

AGC CAC GCC TCC TTG GAC CCT GTG GAG CAG ACT TGC TCC      2028
Ser His Ala Ser Leu Asp Pro Val Glu Gln Thr Cys Ser
    665             670              675

CGG CAA AGC CAG AGC AGC CGA GAG TCC CCG CCA CAG CAG      2067
Arg Gln Ser Gln Ser Ser Arg Glu Ser Pro Pro Gln Gln
            680             685

CAG CCA CCT CGG CTG CCC CCG GAG GTG GAG GCG GGG CAA      2106
Gln Pro Pro Arg Leu Pro Pro Glu Val Glu Ala Gly Gln
690             695             700

CGG CTG CGG GCA GGG CTG CTG CCC TCA CAC CTG CCT GAG      2145
Arg Leu Arg Ala Gly Leu Leu Pro Ser His Leu Pro Glu
        705             710              715

GTG GTG GCC GGC CTC AGC TGC GCC TTC ATC GTG CTG GTC      2184
Val Val Ala Gly Leu Ser Cys Ala Phe Ile Val Leu Val
                720             725

TTC GTC ACT GTC TTC CTG GTC CTG CAG CTG CGC TCT GGC      2223
Phe Val Thr Val Phe Leu Val Leu Gln Leu Arg Ser Gly
        730             735              740

TTT AGT TTT CGG GGG GTG AAG GTG TAC ACC ATG GAC CGT      2262
Phe Ser Phe Arg Gly Val Lys Val Tyr Thr Met Asp Arg
        745             750

GGC CTC ATC TCC TAC AAG GGG CTG CCC CCT GAA GCC TGG      2301
Gly Leu Ile Ser Tyr Lys Gly Leu Pro Pro Glu Ala Trp
755         760                     765

CAG GAG GAG TGC CCG TCT GAC TCA GAA GAG GAC GAG GGC      2340
Gln Glu Glu Cys Pro Ser Asp Ser Glu Glu Asp Glu Gly
        770             775                     780

CGG GGC GAG AGG ACC GCC TTT ATC AAA GAC CAG AGC GCC      2379
Arg Gly Glu Arg Thr Ala Phe Ile Lys Asp Gln Ser Ala
                785             790

CTC TGA TGA GCCCACTGCC CACCCCCTCA AGCCAATCCC CTCCTTGGGC  2428
Leu
```

Fig. 2F

```
ACTTTTTAAT TCACCAAAGT ATTTTTTTAT CTTGGGACTG GGTTTGGACC 2478
CCAGCTGGGA GGCAAGAGGG GTGGAGACTG TTTCCCATCC TACCCTCGGG 2528
CCCACCTGGC CACCTGAGGT GGGCCCAGGA CCAGCTGGGG CGTGGGGAGG 2578
GCCGTACCCC ACCCTCAGCA CCCCTTCCAT GTGGAGAAAG GAGTGAAACC 2628
TTTAGGGCAG CTTGCCCCGG CCCCGGCCCC AGCCAGAGTT CCTGCGGAGT 2678
GAAGAGGGGC AGCCCTTGCT TGTTGGGATT CCTGACCCAG GCCGCAGCTC 2728
TTGCCCTTCC CTGTCCTCT AAAGCAATAA TGGTCCCATC CAGGCAGTCG 2778
GGGGCTGGCC TAGGAGATAT CTGAGGGAGG AGGCCACCTC TCCAAGGGCT 2828
TCTGCACCCT CCACCCTGTC CCCCAGCTCT GGTGAGTCTT GGCGGCAGCA 2878
GCCATCATAG GAAGGGACCA AGGCAAGGCA GGTGCCTCCA GGTGTGCACG 2928
TGGCATGTGG CCTGTGGCCT GTGTCCCATG ACCCACCCCT GTGCTCCGTG 2978
CCTCCACCAC CACTGGCCAC CAGGCTGGCG CAGCCAAGGC CGAAGCTCTG 3028
GCTGAACCCT GTGCTGGTGT CCTGACCACC CTCCCCTCTC TTGCACCCGC 3078
CTCTCCCGTC AGGGCCCAAG TCCTGTTTT CTGAGCCCGG GCTGCCTGGG 3128
CTGTTGGCAC TCACAGACCT GGAGCCCCTG GGTGGGTGGT GGGGAGGGGC 3178
GCTGGCCCAG CCGGCCTCTC TGGCCTCCCA CCCGATGCTG CTTTCCCCTG 3228
TGGGGATCTC AGGGGCTGTT TGAGGATATA TTTTCACTTT GTGATTATTT 3278
CACTTTAGAT GCTGATGATT TGTTTTTGTA TTTTTAATGG GGGTAGCAGC 3328
TGGACTACCC ACGTTCTCAC ACCCACCGTC CGCCTGCTC CTCCCTGGCT 3378
GCCCTGGCCC TGAGGTGTGG GGGCTGCAGC ATGTTGCTGA GGAGTGAGGA 3428
ATAGTTGAGC CCCAAGTCCT GAAGAGGCGG GCCAGCCAGG CGGGCTCAAG 3478
GAAAGGGGGT CCCAGTGGGA GGGGCAGGCT GACATCTGTG TTTCAAGTGG 3528
GGCTCGCCAT GCCGGGGGTT CATAGGTCAC TGGCTCTCCA AGTGCCAGAG 3578
GTGGGCAGGT GGTGGCACTG AGCCCCCCA ACACTGTGCC CTGGTGGAGA 3628
AAGCACTGAC CTGTCATGCC CCCCTCAAAC CTCCTCTTCT GACGTGCCTT 3678
TTGCACCCCT CCCATTAGGA CAATCAGTCC CCTCCCATCT GGGAGTCCCC 3728
TTTTCTTTTC TACCCTAGCC ATTCCTGGTA CCCAGCCATC TGCCCAGGGG 3778
TGCCCCCTCC TCTCCCATCC CCCTGCCCTC GTGGCCAGCC CGGCTGGTTT 3828
TGTAAGATAC TGGGTTGGTG CACAGTGATT TTTTTCTTGT AATTTAAACA 3878
GGCCCAGCAT TGCTGGTTCT ATTTAATGGA CATGAGATAA TGTTAGAGGT 3928
TTTAAAGTGA TTAAACGTGC AGACTATGCA AACCAAAAAA AAAAAAAAAA 3978
ACCGTCGACA AAGCGGCCGC                                3998
```

EXPRESSION OF PACE IN HOST CELLS AND METHODS OF USE THEREOF

REFERENCE TO PRIOR U.S. PATENT APPLICATIONS

This U.S. Patent Application is a Continuation-in-Part of U.S. patent applications Ser. Nos. 07/621,092, filed Nov. 26, 1990, now abandoned; 07/620,859, filed Nov. 29, 1990, now abandoned; 07/621,443, filed Nov. 29, 1990, now abandoned; and 07/621,457, filed Nov. 30, 1990, now abandoned.

BACKGROUND OF THE INVENTION

This invention relates generally to the production of proteins in recombinant host cells. More particularly, it relates to materials and methods for the production of mature forms of proteins from heterologous precursor polypeptides using a paired basic amino acid converting enzyme (PACE), which is expressed in selected host cells.

Many eukaryotic proteins are naturally synthesized as larger precursor polypeptides, which require further specific proteolytic processing for full maturation prior to secretion. However, many of these eukaryotic proteins or precursors when synthesized in bacteria fold incorrectly or inefficiently and, consequently, exhibit low specific activities. Posttranslational proteolysis is frequently required for the synthesis of fully biologically active, mature proteins and peptides in all eukaryotes examined, including yeast [R. S. Fuller et al., *Ann. Rev. Physiol.*, 50:345 (1988)], invertebrates [R. H. Scheller et al., *Cell*, 32:7 (1983)], and mammalian cells [J. Douglass et al., *Ann. Rev. Biochem.*, 53:665 (1984); and W. S. Sossin et al., *Neuron*, 2, 1407 (1989)].

One of the early events in precursor protein maturation is endoproteolytic cleavage at the carboxyl side of paired basic amino acid sequences (e.g., -Lys-Arg- and -Arg-Arg-). This kind of endoproteolytic cleavage was initially inferred from the sequences of several endocrine and neuroendocrine precursor proteins and was first proposed from studies of proinsulin [D. F. Steiner et al., *Science*, 157:697 (1968); R. E. Chance et al., *Science*, 161:165 (1968)] and the ACTH/β-endorphin precursor, proopiomelanocortin (POMC) [M. Chretien and C. H. Li, *Can. J. Biochem.*, 45:1163 (1967)]. Subsequent studies have revealed a broad spectrum of precursor proteins that require endoproteolysis at pairs of basic amino acids to yield mature peptides including serum factors [A. K. Bentley et al, *Cell*, 45:343 (1986)], viral proteins [C. M. Rice et al., *Virology*, 151:1 (1986); C. M. Rice et al., *Science*, 229:726 (1985); J. M. McCune et al., *Cell*, 53:55 (1988)], growth factors [L. E. Gentry et al., *Mol. Cell Biol.*, 8:4162 (1988); K. Sharples et al., *DNA*, 6:239 (1987); M. Yanagisawa et al., *Nature*, 332:411 (1988); and Gray et al., *Nature*, 303:722 (1983)] and receptors [Y. Yosimasa, *Science*, 240:784 (1988)]. See, also, Dickerson et al, *J. Biol. Chem.*, 265:2462 (1990); Achsletter et al, *EMBO J.*, 4:173 (1985); and Mizuno et al, *Biochem. Biophys. Res. Commun.*, 144:807 (1987).

Cleavage at the site of a paired basic amino acid sequence removes many propeptides which function in a variety of roles in the processing of the mature protein. In certain cases the propeptide can mediate correct folding and disulfide bond formation within the protein sequence. In other cases the presence of the propeptide appears to be involved in γ-carboxylation of glutamic acid residues in vitamin K-dependent coagulation factors. γ-carboxylated proteins include Factor IX and Protein C, and certain bone-specific proteins, such as bone Gla protein/osteocalcin. The propeptide can also direct intracellular targeting and regulate the coordinate synthesis of multiple mature peptides from a single precursor polypeptide.

The sequences of the propeptide domains of certain vitamin K-dependent blood coagulation proteins have been published [See, Furie et al, *Cell*, 3:505 (1988)] and the size of the propeptide has been established for both Factor IX and Protein C. Factor IX is a zymogen of a serine protease that is an important component of the intrinsic pathway of the blood coagulation cascade. The protein is synthesized in the liver and undergoes extensive co- and post-translational modification prior to secretion. These modifications involve endoproteolytic processing to remove the pre- and propeptides, glycosylation, vitamin K-dependent γ-carboxylation of 12 amino-terminal glutamic acid residues and β-hydroxylation of a single aspartic acid residue.

The γ-carboxyglutamic acid residues confer metal binding properties on the mature Factor IX protein and may function similarly in the processing of the other vitamin K-dependent blood clotting proteins. These γ-carboxyglutamic acid residues are essential for coagulant activity. The gamma-carboxyglutamate (GLA) domain of Factor IX has also been identified as a major requirement for cell binding [Derian et al, *J. Biol. Chem.*, 264(12):6615–6618 (1989) ].

With the advance of genetic engineering, many eukaryotic proteins are being produced recombinantly in selected cell lines. For example, Chinese Hamster Ovary (CHO) DUKX cell lines producing recombinant Factor IX at high antigen levels (20 µg/ml/day) have been isolated. However, only 1–2% of that recombinant protein is γ-carboxylated, and therefore biologically active, in the presence of vitamin K3 [Kaufman et al, *J. Biol. Chem.*, 261(21):9622–28 (1986)]. Additionally, amino-terminal sequencing of the recombinant protein has found that 50% of the recombinant Factor IX produced by the CHO cells retain the propeptide [Derian et al, *J. Biol. Chem.*, 264(12): 6615–18 (1989)]. Presumably, the endoproteolytic processing enzyme of the CHO cells directing this cleavage was either saturated or simply inefficient in its function.

Several activities capable of cleaving at single or paired basic residues in vitro have been proposed as candidates for authentic mammalian precursor endoproteases. See, for example, Y. P. Loh and H. Gainer, in *Brain Peptides*, D. T. Krieger, M. J. Brownstein, J. B. Martin, Eds. (Wiley-Interscience, New York, 1983), pp.76–116; M. Chretien, et al. in *Cell Biology of the Secretory Process* (Karger, Basel, Switzerland, 1983), pp. 214–246; A. J. Mason, et al., *Nature*, 303:300 (1983); P. J. Isackson et al., *J. Cell. Biochem.*, 33:65 (1987); I. Lindberg et al., *J. Neurochem.*, 42:1411 (1985); J. A. Cromlish et al., *J. Biol. Chem.*, 261:10850 (1986); K. Docherty et al., *J. Biol. Chem.*, 259:6041 (1984); T. C. Chang and Y. P. Loh, *Endocrinology*, 114, 2092 (1984); B. P. Noe et al., *J. Cell. Biol.*, 99:578 (1984); U. P. Loh, *J. Biol. Chem.*, 261:11949 (1986); H. W. Davidson et al., *Biochem. J.*, 246:279 (1987); P. Gluschankof et al., *J. Biol. Chem.*, 262:9615 (1987); C. Clamigrand et al., *Biochem.*, 26:6018 (1987); S. O. Brennan and R. J. Peach, *FEBS Letters*, 229:167 (1988); R. S. Fuller et al., *Proc. Natl. Acad. Sci. USA*, 86:1434 (1989); K. Mizuno et al., *Biochem. Biophys. Res. Comm.*, 159:305 (1989); I. C. Bathurst et al., *Science*, 235:348 (1987); and G. Thomas et al., *Science*, 241:226 (1988)].

Despite the fact that these candidate activities and other processing enzymes have been proposed as being involved in the propeptide processing reactions, these endoproteolytic candidates have either not been fully characterized or have not been shown to be a bona fide precursor cleaving endoprotease in vivo. The purification of proprotein cleavage enzymes has been hampered by their low levels of activity in mammalian tissue and by their membrane-associated nature. Purification of these specific proteases has been complicated additionally by non-specific cleavage of the assay substrates in vitro, and by contaminating proteases such as those released from lysosomes.

The yeast enzyme Kex2, encoded by the KEX2 gene, is a membrane-bound, $Ca^{++}$-dependent serine protease which functions late in the secretory pathway of Saccharomyces cerevisiae. The enzyme cleaves the polypeptide chains of prepro-killer toxin and prepro-α-factor of that microorganism at the paired basic amino acid sequences of Lys-Arg and Arg-Arg [D. Julius et al, *Cell.*, 37:1075 (1984); D. Julius et al, *Cell.*, 36:309 (1984); K. Mizuno et al., *Biochem. Biophys. Res. Commun.*, 156:246 (1988); R. S. Fuller et al., *Proc. Natl. Acad. Sci. USA*, 86:1434 (1989)]. Kex-2 has been considered to be a prototypic proprotein convertase.

Recently, co-expression of the yeast KEX2 gene with POMC in mammalian BSC-40 cells (a cell line which is incapable of processing this peptide precursor) reportedly resulted in the generation, by proteolytic cleavage at pairs of basic amino acids, of authentic neuroendocrine prohormone peptides, including γ-LPH and β-endorphin [Thomas et al, (1988), cited above]. Foster et al, *Thrombosis and Haemostasis*, 62:321 (1989) have reported that the yeast KEX2 gene product cleaves the Protein C precursor to a two-chain form when the yeast endoprotease of the KEX2 gene and the wild-type Protein C precursor are coexpressed. However, propeptide processing and the effect of Kex2 expression have not been studied.

Two human DNA protease sequences, designated PC2 and fur, share some structural homology with each other and with the KEX2 gene sequence. PC2, a mammalian subtilisin-like protease, was identified by amplification of a human insulinoma cDNA library by the polymerase chain reaction using KEX2-derived primers. PC2, which has been implicated in the endoproteolytic processing of prohormones, shares a partial homology to the yeast Kex2 protease, especially in the putative active site domains [Smeekens et al, *J. Biol. Chem.*, 265:2997 (1990)]. To date, however, no functional activity has been demonstrated for the PC2 clone.

The availability of the complete Kex2 gene sequence also allowed the detection of significant homology between the Kex2 protein and "furin", the product of the partially characterized human fur gene. The fur locus was initially identified by its proximity (in the immediate upstream region) to the c-fes/fps proto-oncogene [A. J. M. Roebroek et al, *EMBO J.*, 5:2197 (1986)]. The complete nucleotide sequence of the putative coding region of the fur gene has been reported. Upon comparison, the human fur gene product has demonstrated structural homology with the subtilisin-type serine protease encoded by the KEX2 gene of the yeast *S. cerevisiae* [A. M. W. van den Ouweland et al, *Nucl. Acids Res.*, 18(3):664 (1990). This published cDNA coding sequence for fur is presented in FIG. 1 [SEQ ID NO: 1]. See, also, R. S. Fuller et al, *Science*, 246:482 (1989). However, no evidence of the expression of fur was reported.

An expression system has been developed which utilizes baculovirus vectors to introduce heterologous genes into insect cells in culture and subsequently effects the expression of the heterologous polypeptide. This has proven successful for the recombinant expression of some proteins [see, e.g., G. Ju et al., *Curr. Communic. in Mol. Biol.—Gene Transfer Vectors for Mammalian Cells*, C.S.H.L. Press (1987) pps. 39–45; and A. E. Atkinson et al., *Pestic. Sci.*, 28:215–224 (1990) ].

There remains a need in the art for a method of increasing the efficiency of proteolytic processing of precursor polypeptides in recombinant host cells.

SUMMARY OF THE INVENTION

In one aspect, the present invention provides a selected host cell comprising a recombinant polynucleotide encoding PACE, which cell is capable of expressing PACE. In various embodiments of this aspect of the invention, the host cell may be a microorganism, e.g., a bacterial or fungal cell, a mammalian cell or an insect cell.

In a further aspect, the invention provides a selected host cell comprising a recombinant polynucleotide encoding PACE and a heterologous polynucleotide encoding a selected precursor polypeptide. The selected precursor polypeptide is preferably a substrate for the encoded PACE. This host cell is characterized by the ability to express both PACE and the heterologous precursor protein, which is then cleaved by the co-expressed PACE into its mature form. This host cell is thereby capable of producing high levels of PACE and the active, mature heterologous protein. In various embodiments of this aspect of the invention, the host cell may be a microorganism, e.g., a bacterial or fungal cell, a mammalian cell or an insect cell.

In another aspect, the present invention provides a recombinant expression vector or DNA molecule comprising a polynucleotide sequence encoding PACE or a homolog thereof. The vector preferably provides the sequence encoding PACE operably linked to a regulatory sequence capable of directing the replication and expression of PACE in a selected host cell.

In still another aspect, the recombinant expression vector or a DNA molecule of this invention further comprises a polynucleotide sequence encoding a precursor polypeptide, which is a substrate for PACE. The coding sequences of the vector are operably linked with one or more suitable regulatory sequences capable of directing the replication and expression of PACE and the selected propeptide in a selected host cell.

In still a further aspect the invention provides a method for expressing PACE in a selected host cell, described above, which comprises culturing the selected cell comprising a PACE-encoding polynucleotide under conditions suitable for expressing PACE.

In yet another aspect the invention provides a method for expressing PACE and a heterologous polypeptide in a selected host cell which comprises culturing a selected above-described cell comprising a PACE polynucleotide and a heterologous polynucleotide encoding a selected precursor polypeptide under suitable conditions permitting expression of both PACE and the heterologous polypeptide. This method may increase the efficiency of, or otherwise enhance the production of, a functional, mature protein, which protein requires processing by the enzyme PACE of a propeptide form for biological activity. The invention may also be used for the processing of γ-carboxylated proteins and other proteins not requiring gamma carboxylation, leading to higher levels of biologically active or otherwise useful proteins.

The method may involve transforming a selected host cell with the recombinant expression vectors described above. This cell line is then cultured under appropriate conditions permitting expression of the recombinant protein(s). The expressed selected protein(s) is then harvested from the host cell or culture medium by suitable conventional means.

Other aspects and advantages of this invention are apparent from the following detailed description of the invention.

DESCRIPTION OF THE DRAWING

FIG. 1 [SEQ ID NO: 1]illustrates the published fur DNA sequence of A.M. W. van den Ouweland et al, *Nucl. Acids Res.*, 18(3):664 (1990).

FIG. 2 [SEQ ID NO: 3] illustrates the composite cDNA sequence encoding PACE, and the amino acids encoded therein, which differs from the above FIG. 1 in the inclusion of the 5' untranslated region from nucleotide #-320 to -1, and the 3' untranslated region from nucleotide #2383 to 3974.

DETAILED DESCRIPTION OF THE INVENTION

The present invention includes compositions (e.g., vectors, transformed host cells, recombinant polypeptides) and methods for producing, expressing, and also secreting, in selected host cells a mammalian endopeptidase, PACE, which is involved in the production of mature polypeptides from precursor polypeptides by cleavage at pairs of basic amino acids (-LysArg-, -LysLys-, and -ArgArg-). The compositions of the present invention, e.g., the recombinant polynucleotides, can be used for enhanced intracellular or extracellular production of PACE in various host cells, including microorganisms, e.g., bacteria and fungi; insect cells and mammalian cells. The production of PACE in these expression systems provides another embodiment of this invention, methods for the efficient processing and conversion of co-expressed heterologous precursor polypeptides having processing sites recognized by the PACE endopeptidase to desired mature forms of those polypeptides. The compositions of this invention are also useful for the production of the endopeptidase in high yields for production of purified endopeptidase for commercial purposes.

The practice of the present invention employs, unless otherwise indicated, conventional techniques of molecular biology, microbiology, recombinant DNA, and immunology, which are within the skill of the art. Such techniques are explained fully in the literature. See, e.g., Sambrook, et al., "Molecular Cloning; A Laboratory Manual", 2nd ed (1989); "DNA Cloning", Vols. I and II (D. N Glover ed. 1985); "Oligonucleotide Synthesis" (M. J. Gait ed. 1984); "Nucleic Acid Hybridization" (B. D. Hames & S. J. Higgins eds. 1984); "Transcription and Translation" (B. D. Hames & S. J. Higgins eds. 1984); "Animal Cell Culture" (R. I. Freshney ed. 1986); "Immobilized Cells and Enzymes" (IRL Press, 1986); B. Perbal, "A Practical Guide to Molecular Cloning" (1984); the series, *Methods in Enzymology* (Academic Press, Inc.), particularly Vols. 154 and 155 (Wu and Grossman, and Wu, eds., respectively); "Gene Transfer Vectors for Mammalian Cells" (J. H. Miller and M. P. Calos eds. 1987, Cold Spring Harbor Laboratory); "Immunochemical Methods in Cell and Molecular Biology", Mayer and Walker, eds. (Academic Press, London, 1987); Scopes, "Protein Purification: Principles and Practice", 2nd ed. 1987 (Springer-Verlag, N.Y.); and "Handbook of Experimental Immunology" Vols I–IV (D. M. Weir and C. C. Blackwell eds 1986). All patents, patent applications, and publications cited in the background and specification are incorporated herein by reference.

The following definitions may be applied to terms employed in the description of embodiments of the invention. As used herein, the term "PACE" is an acronym for paired basic amino acid converting (or cleaving) enzyme. PACE, originally isolated from a human liver cell line, is a subtilisin-like endopeptidase, i.e., a propeptide-cleaving enzyme which exhibits specificity for cleavage at basic residues of a polypeptide, e.g., -Lys-Arg-, -Arg-Arg-, or -Lys-Lys-. PACE is stimulated by calcium ions; and inhibited by phenylmethyl sulfonyl fluoride (PMSF). A DNA sequence encoding PACE (or furin) was published in A.M.W. van den Ouweland et al, cited above, and appears in FIG. 1 [SEQ ID NO: 1].

A cDNA encoding at least one form of PACE, derived from an animal cell, more specifically from a human cell, is presented in FIG. 2 [SEQ ID NO: 3]. It is anticipated that other forms of PACE exist or that they can be created. PACE, as described herein, may be encoded by DNA sequences that differ in sequence from the published sequence and the sequence of FIG. 2 [SEQ ID NO: 3] due to natural allelic or species variations. Thus, the term "PACE" refers to any of the naturally occurring forms of PACE, including the PACE precursor shown in FIG. 2 [SEQ ID NO: 3] and various processed forms, including the mature PACE polypeptide.

Similarly the term PACE may include fragments of the PACE DNA and amino acid sequences or deliberately modified sequences thereof that maintain the catalytic specificity of that enzyme. Therefore, provided that the biological activities of mediating propeptide cleavage and/or γ-carboxylation are retained in whole or part despite such modifications, this invention encompasses the use of all such DNA sequences. The term "PACE" as used herein thus encompasses the peptide and DNA sequences specifically disclosed herein as well as analogs thereof retaining PACE biological activity.

Analogs of PACE included within the definition may include truncated polypeptides (including fragments) and PACE-like polypeptides, e.g., mutants, that retain catalytic activity and preferably have a homology to FIG. 1 [SEQ ID NO: 1] or 2 [SEQ ID NO: 3] of at least 80%, more preferably 90%, and most preferably 95%. Typically, such analogs differ by only 1, 2, 3, or 4 codon changes. Examples include polypeptides with minor amino acid variations from the natural amino acid sequence of PACE; in particular, conservative amino acid replacements. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on the enzymatic activity, especially if the replacement does not involve an amino acid at the active site of the PACE-like polypeptide.

Utilizing the sequence data in FIG. 2 [SEQ ID NO: 3], as well as the denoted characteristics of PACE, it is within the skill of the art to obtain other DNA sequences encoding PACE. For example, the structural gene may be manipulated by varying individual nucleotides, while retaining the correct amino acid(s), or varying the nucleotides, so as to modify the amino acids, without loss of enzymatic activity. Nucleotides may be substituted, inserted, or deleted by known techniques, including, for example, in vitro mutagenesis and primer repair.

The structural gene may be truncated at its 3'-terminus and/or its 5'-terminus while retaining its endopeptidase activity. For example, PACE as encoded in FIG. 2 [SEQ ID NO: 3] contains a putative transmembrane domain which may serve to anchor it in the membranes of the Golgi in the cell in which it is expressed. Additionally, it may be desirable to delete the transmembrane (TM) region and/or the cysteine-rich region (CRR). It also may be desirable to remove the region encoding the signal sequence, and/or to replace it with a heterologous sequence.

It may also be desirable to ligate a portion of the PACE sequence (particularly that which includes the catalytic domain) to a heterologous coding sequence, and thus to create a fusion peptide with the enzymatic specificity of PACE.

In addition to the above, other open reading frames (ORFs) or structural genes encoding PACE may be obtained and/or created from cDNA libraries from other animal cell sources.

As used herein, the term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

The term "precursor polypeptide" denotes an expressed polypeptide which normally undergoes one or more post-translational proteolytic cleavages to yield a biologically active mature polypeptide. Included within the term "precursor polypeptide" are "prepropolypeptides" and "propolypeptides."

A "prepeptide" is the portion of a precursor polypeptide which is removed by "signal peptidase" cleavage during translocation of the polypeptide into the endoplasmic reticulum. The "prepeptide" region is usually at or near the amino terminus.

A "propeptide" is the portion of a precursor polypeptide which is removed by a "propolypeptide convertase" or "endopeptidase" (for example, Kex2 and PACE) during the maturation process of the polypeptide. Many proteins, such as plasma proteins, hormones, neuropeptides, and growth factors, are translated with an additional "propeptide" region located to the carboxy side of the prepeptide region. After cleavage of the prepeptide, the "propeptide" segment is cleaved by a site-specific endopeptidase contributing to the maturation of the polypeptide. A "mature" form of a polypeptide has had a prepeptide and/or propeptide region removed.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

A recombinant or derived polypeptide is not necessarily translated from a designated nucleic acid sequence, for example, the sequence in FIG. 2 [SEQ ID NO: 3]. It may be generated in any manner, including for example, chemical synthesis, or expression of a recombinant expression system, or isolation from a cell. A recombinant or derived polypeptide may include one or more analogs of amino acids or unnatural amino acids in its sequence. Methods of inserting analogs of amino acids into a sequence are known in the art. It also may include one or more labels, which are known to those of skill in the art.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps" substitution of one or more of the naturally occurring nucleotides with an analog. Other known modifications include internucleotide modifications, for example, those with uncharged linkages (methyl phosphonates, phosphotriesters, phosphoamidates, carbamates, etc.) and with charged linkages (phosphorothioates, phosphorodithioates, etc.), those containing pendant moieties, such as, proteins (including nucleases, toxins, antibodies, signal peptides, poly-L-lysine, etc.), those with intercalators (acridine, psoralen, etc.), those containing chelators (metals, radioactive metals, boron, oxidative metals, etc.), those containing alkylators, those with modified linkages (alpha anomeric nucleic acids, etc.), as well as unmodified forms of the polynucleotide.

A "replicon" is any genetic element that behaves as an autonomous unit of polynucleotide replication within a cell, that is, capable of replication under its own control. Thus a replicon may include, without limitation, a selectable marker, a plasmid, a chromosome, a virus, a cosmid.

A "vector" is a replicon in which another polynucleotide segment is attached, so as to bring about the replication and/or expression of the attached segment.

A "Control sequence" or "Regulatory sequence" refers to polynucleotide sequences which are necessary to effect the replication and expression of coding sequences to which they are ligated. The nature of such control sequences differs depending upon the host organism. In prokaryotes, such control sequences generally include promoter, ribosomal binding site, and transcription termination sequences. In eukaryotes, generally, such control sequences include promoters and transcription termination sequences. The term "control sequences" is intended to include, at a minimum, all components whose presence is necessary for expression in a selected host cell, and may also include additional components whose presence is advantageous, for example, leader sequences and fusion partner sequences.

"Operably linked" or related terms such as "operative association" refer to the relationship between the components so described which permits them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide. This region may represent a portion of a coding sequence or a total coding sequence.

A "coding sequence" is a polynucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, cDNA, and recombinant polynucleotide sequences.

"PCR" refers to the technique of polymerase chain reaction as described in Saiki et al., *Nature*, 324:163 (1986); U.S. Pat. No. 4,683,195; and U.S. Pat. No. 4,683,202. Other known PCR modifications are also included by use of this acronym.

As used herein, x is "heterologous" with respect to y if x is not naturally associated with y in the identical manner; i.e., x is not associated with y in nature or x is not associated with y in the same manner as is found in nature.

"Recombinant host cells", "host cells", "cells", "cell lines", "cell cultures", and other such terms denote selected host cells, e.g., mammalian, insect or microorganism cells, that can be, or have been, used as recipients for a recombinant vector or other transfer DNA. These terms include the progeny of the original cell which has been transformed. It is understood that the progeny of a single parental cell may not necessarily be completely identical in morphology or in genomic or total DNA complement as the original parent, due to natural, accidental, or deliberate mutation.

As used herein, the term "microorganism" includes prokaryotic and eukaryotic microbial species such as bacteria and fungi. Fungi include yeast and filamentous fungi. The term "microorganism" specifically excludes mammalian cells and insect cells.

"Mammalian cells" are cells that are from a member of the Class Mammalia, and specifically exclude microorganism cells and insect cells.

Insect cells and compatible vectors which are useful as recombinant expression systems are known in the art. Examples include insect expression and transfer vectors derived from the baculovirus *Autographa californica* nuclear polyhedrosis virus (hereinafter "AcNPV" or "baculovirus"), which is a helper-independent, viral expression vector. Viral expression vectors derived from this system usually use the strong viral polyhedrin gene promoter to drive expression of heterologous genes.

"Transformation", as used herein, refers to the insertion of an exogenous polynucleotide into a host cell, irrespective of the method used for the insertion. Examples include direct uptake, transfection, f-mating, transduction, infection or electroporation. The exogenous polynucleotide may be maintained as a non-integrated vector, for example, a plasmid, or alternatively, may be integrated into the host genome.

The inventors have discovered that the enzyme PACE may be recombinantly expressed in a variety of host cells, including mammalian cells, microorganisms and insect cells. One method of this invention employs a single transformed host cell expressing PACE. A polynucleotide sequence encoding PACE or a biologically active fragment thereof may be inserted into an expression vector and operably linked to expression control sequences suitable for expression of the enzyme in the selected host cell. Transformation or transfection of the vector into the selected host cell can be effected using materials and methods conventional for introducing polynucleotides into a host cell. Among such methods are packaging the polynucleotide in a virus and transducing a host cell with the virus or by transfection procedures known in the art, as exemplified by U.S. Pat. Nos. 4,399,216; 4,912,040; 4,740,461; 4,959,455 (these patents are incorporated herein by reference). The transformation procedure used depends upon the host to be transformed. Once the vector is transformed into the selected host cell, the cell is cultured to express PACE.

In order to obtain PACE expression, recombinant host cells derived from the transformants are incubated under conditions which allow expression of the recombinant PACE encoding sequence. These conditions will vary, dependent upon the host cell selected. However, the conditions are readily ascertainable to those of ordinary skill and knowledge in the art.

Detection of PACE expressed in the transformed host cell may be by several methods. For example, detection can be by enzymatic activity (or increased enzymatic activity or increased longevity of enzymatic activity) using fluorogenic substrates which are comprised of a dibasic cleavage site for which PACE is specific. PACE may also be detected by its immunological reactivity with anti-PACE antibodies.

PACE may be isolated from the cell by lysis, if formed intracellularly, or isolated from the culture medium, if secreted, by conventional methods. If the transmembrane domain is retained during expression so that the PACE localizes in the host cell membranes, the host cells may be lysed and the membrane fragments isolated by conventional techniques. These fragments containing enriched amounts of PACE may be used as is, or fixed to a solid substrate for use in processing precursor polypeptides. The cell membranes may be dispersed in a medium at optimal pH, or particle bound membrane may be packed in a column. Other useful configurations may also be employed.

Recombinantly expressed PACE can improve the efficiency of cleavage of a precursor polypeptide between the dibasic residues Lys-Arg, Lys-Lys or Arg-Arg into its mature form. Thus another embodiment of this invention is provided by the action of recombinantly-expressed PACE on selected precursor polypeptides, either recombinant or naturally occurring. The expressed precursor will be one which has a processing site recognized by PACE.

As one example, the recombinantly-expressed PACE may be used for the in vitro conversion of heterologous precursor polypeptides to mature polypeptides. Soluble recombinant PACE, i.e., a truncated PACE polypeptide lacking a transmembrane domain, may be used as an added reagent to extracellular (or conditioned) media where a precursor product is secreted from the cell in which it is expressed.

More preferably, the co-expression of PACE and a proprotein which requires such processing for production of the mature protein is an embodiment of this invention, which can result in high level expression of the mature protein. Additionally, the inventors have also surprisingly discovered that co-expression of PACE with proteins requiring γ-carboxylation for biological activity permits the expression of increased yields of functional, biologically active mature proteins in eukaryotic, preferably mammalian, cells.

Examples of precursor polypeptides for use in the present invention include, but are not limited to, transforming growth factor (TGF) beta and its superfamily, including inhibin and activin; bone morphogenic proteins (BMP); insulin and relaxin; coagulation factors, such as von Willebrand factor (vWF); Factor IX, Protein C, Protein S, Prothrombin Factor X, Factor VII and bone gamma-carboxyglutamate protein, growth factors, such as platelet derived growth factor (PDGF) and nerve growth factor (NGF); and virus polypeptides, including those from cytomegalovirus (CMV), hepatitis delta virus (HDV), hepatitis C virus (HCV), human immunodeficiency virus (HIV), and herpes simplex virus (HSV). Any precursor polypeptide with at least one dibasic cleavage site is a candidate for the present invention.

Methods for producing a desired mature polypeptide by co-expression with PACE can include the following techniques. First, a single vector containing coding sequences for both PACE and the heterologous precursor polypeptide can be inserted into a selected host cell. Alternatively, two separate vectors coding, respectively, for PACE and the heterologous precursor polypeptide, can be inserted into a host. Upon culturing under suitable conditions for the selected host cell, the two polypeptides are produced and interact to provide cleavage of the proprotein into the mature protein.

Another alternative is the use of two transformed host cells wherein one host cell expresses soluble recombinant PACE and the other host cell expresses the heterologous precursor polypeptide which will be secreted into the medium. These host cells can be co-cultured under conditions which allow expression and secretion or release of the recombinant PACE, as well as expression, secretion or release of the precursor polypeptide, and its cleavage into the mature form by the extracellular PACE. In this method, it is preferred that the PACE polypeptide lacks the transmembrane domain so that it secretes into the medium.

In some instances, it may be desirable to have a plurality of copies, two or more, of the gene expressing the expression product precursor in relation to the PACE gene, or vice versa. This can be achieved in a variety of ways. For example, one may use separate vectors or plasmids, where the vector containing the PACE encoding polynucleotide has a higher copy number than the vector containing the polynucleotide sequence encoding the heterologous precursor polypeptide, or vice versa. In this situation, it would be desirable to have different markers on the two plasmids, so as to ensure the continued maintenance of the plasmids in the host. Alternatively, one or both genes could be integrated into the host genome, and one of the genes could be associated with an amplifying gene, (e.g., dhfr or one of the metallothionein genes).

Alternatively, one could employ two transcriptional regulatory regions having different rates of transcriptional initiation, providing for the enhanced expression of either the PACE gene or the expression of the precursor polypeptide, relative to the other gene. As another alternative, one can use different promoters, where one promoter provides for a low level of constitutive expression of either PACE or the precursor polypeptide, while the second promoter provides for a high level of induced expression of the other product. A wide variety of promoters are known for the selected host cells, and can be readily selected and employed in the invention by one of skill in the art.

By use of these methods, the natural level of PACE may be greatly enhanced and/or the longevity of protease activity may be increased, so as to more efficiently process the expression product precursor.

A. Mammalian Expression of PACE

The methods of the present invention may be performed by inserting a polynucleotide sequence encoding PACE or a fragment thereof into a suitable mammalian expression vector. The vector containing PACE is then transformed into a selected mammalian cell line. The establishment of cell lines which express PACE provides a convenient and efficient mechanism for the high level production of PACE, as well as for the production of more completely processed and biologically active proteins.

Where the method involves the co-expression of PACE and a precursor polypeptide, a single vector can carry the PACE DNA and another vector can carry the selected precursor DNA, each under the control of a selected expression control sequence. Alternatively, both the PACE and precursor DNA sequences may be carried on a single recombinant vector molecule in which case they may be operably linked to respective expression control sequences or may share a common expression control sequence. As another alternative, a vector containing the PACE DNA may be transfected into a host cell line known to express the desired proprotein, or a vector containing the DNA for the desired protein may be transfected into a cell known to express PACE.

Vector construction employs techniques which are known in the art. Site-specific DNA cleavage involved in such construction is performed by treating with suitable restriction enzymes under conditions which generally are specified by the manufacturer of these commercially available enzymes.

A suitable expression vector is one that is compatible with the desired function (e.g., transient expression, long term expression, integration, replication, amplification) and in which the control elements are compatible with the host cell. In general, the vectors employed will contain selected regulatory sequences operably linked with the DNA coding sequences of PACE and selected precursor and capable of directing the replication and expression thereof in selected host cells.

Vectors suitable for replication in mammalian cells may include viral replicons, or sequences that ensure integration of the sequence encoding PACE into the host genome. Suitable vectors may include, for example, those derived from simian virus SV40, retroviruses, bovine papilloma virus, vaccinia virus, and adenovirus. The components of the vectors, e.g. replicons, selection genes, enhancers, promoters, and the like, may be obtained from natural sources or synthesized by known procedures. [See, Kaufman et al, *J. Mol. Biol.*, 159:511–521 (1982); and Kaufman, *Proc. Natl. Acad. Sci., USA*, 82:689–693 (1985)].

A suitable vector, for example, is one derived from vaccinia viruses. In this case, the heterologous DNA is inserted into the vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker. Plasmid shuttle vectors that greatly facilitate the construction of recombinant viruses have been described [see, for example, Mackett et al. (1984), Chakrabarti et al. (1985); Moss (1987)]. Expression of the heterologous polypeptide then occurs in cells or individuals which are immunized with the live recombinant vaccinia virus.

Suitable mammalian expression vectors usually contain one or more eukaryotic transcription units that are capable of expression in mammalian cells. The transcription unit is comprised of at least a promoter element to mediate transcription of foreign DNA sequences. Suitable promoters for mammalian cells are known in the art and include viral promoters such as that from simian virus 40 (SV40), cytomegalovirus (CMV), Rous sarcoma virus (RSV), adenovirus (ADV), and bovine papilloma virus (BPV).

In addition, the transcription unit may also be comprised of a termination sequence and poly(A) addition sequences which are operably linked to the PACE and/or precursor coding sequence(s). The transcription unit may also be comprised of an enhancer sequence which increases the expression of PACE and/or the precursor.

The optional presence of an enhancer element (enhancer), combined with the promoter elements described above, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when they are placed upstream or downstream from the transcription initiation site, in either normal or flipped orientation, or at a distance of more than 1000 nucleotides from the promoter [Maniatis et al. *Science,* 236:1237 (1987); Alberts et al., *Molecular Biology of the Cell,* 2nd ed. (1989)]. Enhancer elements derived from viruses may be particularly useful, because they typically have a broader host range. Examples include the SV40 early gene enhancer [Dijkema et al, *EMBO J.,* 4:761 (1985)] and the enhancer/promoters derived from the long terminal repeat (LTR) of the Rous Sarcoma Virus [Gorman et al., *Proc. Natl. Acad. Sci.* 79:6777 (1982b)] and from human cytomegalovirus [Boshart et al., *Cell,* 41:521 (1985)]. Additionally, some enhancers are regulatable and become active only in the presence of an inducer, such as a hormone or metal ion [Sassone-Corsi and Borelli, *Trends Genet.* 2:215 (1986); Maniatis et al. Science, 236:1237 (1987)].

Sequences which cause amplification of the gene may also be desirable, as are sequences which encode selectable markers. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin.

Alternatively, the vector DNA may include all or part of the bovine papilloma virus genome [Lusky et al, *Cell,* 36:391–401 (1984)] and be carried in cell lines such as C127 mouse cells as a stable episomal element.

The vector used in the examples below is pMT3, a derivative of the previously described vector pMT2 [R. Kaufman, *Mol. Cell. Biol.,* 9:946–958 (1989)]. One skilled in the art can also construct other mammalian expression vectors comparable to the pMT3/PACE vector (see Example 1) by, e.g. inserting the DNA sequence of PACE from pMT3 into another vector, such as pJL3, pJL4 [Gough et al., *EMBO J.,* 64:45–653 (1985)], employing well-known recombinant genetic engineering techniques. The mammalian cell expression vectors described herein may be synthesized by techniques well known to those skilled in this art. Other appropriate expression vectors of which numerous types are known in the art for mammalian expression can also be used for this purpose.

One or more selected vector(s) encoding PACE and/or the precursor polypeptide can be used for transformation of a suitable mammalian host cell. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC). Exemplary mammalian host cells include particularly primate cell lines and rodent cell lines, including transformed cell lines. Preferably for stable integration of the vector DNA, and for subsequent amplification of the integrated vector DNA, both by conventional methods, Chinese hamster ovary (CHO) cells are employed as a mammalian host cell of choice. Other suitable cell lines include, but are not limited to, HeLa cells, baby hamster kidney (BHK) cells, monkey kidney cells (COS-1), human hepatocellular carcinoma cells (e.g., Hep G2), human adenovirus transformed 293 cells, mouse L-929 cells, HaK hamster cell lines, murine 3T3 cells derived from Swiss, Balb-c or NIH mice and a number of other cell lines. Another suitable mammalian cell line is the CV-1 cell line. Normal diploid cells, cell strains derived from in vitro culture of primary tissue, as well as primary explants, are also suitable. Candidate cells may be genotypically deficient in the selection gene, or may contain a dominantly acting selection gene.

The selection of suitable mammalian host cells and methods for transformation, culture, amplification, screening and product production and purification are known in the art. See, e.g., Gething and Sambrook, *Nature,* 293:620–625 (1981), or alternatively, Kaufman et al, *Mol. Cell. Biol.,* 5(7):1750–1759 (1985) or Howley et al, U.S. Pat. No. 4,419,446.

The host cells transformed with the one or more vectors carrying the PACE DNA and the selected precursor DNA are selected, e.g. by conventional means, and may then be cultured under suitable conditions if desired, with amplification of one or both introduced genes. The method of this present invention therefore comprises culturing a suitable cell or cell line, which has been transformed with a DNA sequence coding for PACE and a DNA sequence coding for the selected precursor, each coding sequence under the control of a transcriptional regulatory sequence. The expressed mature protein is then recovered, isolated and purified from the culture medium (or from the cell, if expressed intracellularly) by appropriate means known to one of skill in the art.

With respect to γ-carboxylated proteins, it is presently and theoretically contemplated that the expression of PACE in mammalian cells increases the efficiency of γ-carboxylation, a post-translational modification required for biological activity of certain mature proteins. The method is especially useful in the processing of vitamin K-dependent blood coagulation proteins. More specifically the method is useful in processing and γ-carboxylating other proteins including Protein C, Protein S, Prothrombin Factor IX, Factor VII, Factor X and bone γ-carboxyglutamate protein. For example, co-expression with PACE with such a propeptide permits high level recombinant expression of biologically active mature proteins.

In addition, high levels of recombinant expression of functional proteins can also be achieved by use of the present method by expressing PACE with more completely processed proteins expressed from other genes. For example, coexpression of PACE with non-Vitamin K dependent propeptides which require cleavage, but not γ-carboxylation, for biological activity may produce high yields of functional mature proteins.

One such protein which may be expressed in high functional yields by the present method is bone morphogenic protein (BMP), particularly BMP-2 [see, e.g., E. Wang et al, *Proc. Natl. Acad. Sci. USA*, 87:2220–2224 (1990), which is incorporated by reference herein for information about that protein]. Other such proteins which may be produced in high functional yields by the present invention include tumor growth factor β (TGF-β) and platelet-derived growth factor (PDGF) and the precursors identified specifically above.

Further, the present invention also encompasses the use of recombinant-derived PACE for in vitro processing of nerve growth factor and monobasic propiomelanocortin. PACE may also be useful in the processing of proteins, such as insulin, and for the maturation of viruses, such as HIV and Hepatitis C, which also require precursor processing at paired basic amino acid residues.

While mammalian cells are preferred as hosts for the co-expression of PACE and a mammalian proprotein, it is anticipated that microorganism and insect cells may be suitable hosts for such expression of PACE and mammalian proproteins, as well as expression, where desired of proproteins of microbial or insect origin.

B. Expression of PACE in Microorganism Cells

The PACE gene or a fragment thereof can be expressed in a eukaryotic or prokaryotic microorganism system, such as fungi, including yeast, or bacteria. Fragments can include truncated forms of the PACE gene. Examples of truncation include, but are not limited to, deletion of the transmembrane region and/or the cysteine-rich region.

Fungal expression systems can utilize both yeast and filamentous fungi hosts. Examples of filamentous fungi expression systems are Aspergillus, as described in EPO Pub. No. 357 127 (published Mar. 7, 1990), and *Acremonium chrysogenum*, described in EPO Pub. No. 376 266 (published Jul. 4, 1990).

A yeast expression system can typically include one or more of the following: a promoter sequence, fusion partner sequence, leader sequence, transcription termination sequence. These elements can be combined into an expression cassette, which may be maintained in a replicon, preferably with a selectable marker.

A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (E.P.O. Pub. No. 284044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (E.P.O. Pub. No. 329203). The yeast PHO5 gene, encoding acid phosphatase, also provides useful promoter sequences [Myanohara et al., *Proc. Natl. Acad. Sci. USA*, 80:1 (1983)].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region [U.S. Pat. Nos. 4,876,197 and 4,880,734]. Other examples of hybrid promoters include promoters which consist of the regulatory sequences of either the ADH2, GAL4, GAL10, or PHO5 genes, combined with the transcriptional activation region of a glycolytic enzyme gene such as GAP or PyK [E.P.O. Pub. No. 164556]. Furthermore, a yeast promoter can include naturally occurring promoters of non-yeast origin that have the ability to bind yeast RNA polymerase and initiate transcription. Examples of such promoters include, inter alia, [Cohen et al., *Proc. Natl. Acad. Sci. USA*, 77:1078 (1980); Henikoff et al., *Nature* 283:835 (1981); Hollenberg et al., *Curr. Topics Microbiol. Immunol.*, 96:119 (1981); Hollenberg et al., "The Expression of Bacterial Antibiotic Resistance Genes in the Yeast Saccharomyces cerevisiae," in: *Plasmids of Medical, Environmental and Commercial Importance* (eds. K. N. Timmis and A. Puhler, 1979); Mercereau-Puigalon et al., *Gene*, 11:163 (1980); and Panthier et al., *Curr. Genet.*, 2:109 (1980)].

The PACE gene or a fragment thereof may be expressed intracellularly in yeast. A promoter sequence may be directly linked with the PACE gene or fragment, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Intracellularly expressed fusion proteins provide an alternative to direct expression of the PACE gene or fragment. Typically, a DNA sequence encoding the N-terminal portion of a stable protein, a fusion partner, is fused to the 5' end of heterologous DNA encoding the desired polypeptide. Upon expression, this construct will provide a fusion of the two amino acid sequences. For example, the yeast or human superoxide dismutase (SOD) gene, can be linked at the 5' terminus of the PACE gene or fragment thereof and expressed in yeast. The DNA sequence at the junction of the two amino acid sequences may or may not encode a cleavable site. See, e.g., E.P.O. Pub. No. 196056. Another example is a ubiquitin fusion protein. Such a ubiquitin fusion protein preferably retains a site for a processing enzyme (e.g. ubiquitin-specific processing protease) to cleave the ubiquitin from the PACE polypeptide. Through this method, therefore, a mature PACE polypeptide can be isolated [see, P.C.T. WO 88/024066].

Alternatively, PACE polypeptides can also be secreted from the cell into the growth media by creating chimeric DNA molecules that encode a fusion protein comprised of a leader sequence fragment that provides for secretion in yeast of the PACE polypeptides. Preferably, there are processing sites encoded between the leader fragment and the PACE gene or fragment thereof that can be cleaved either in vivo or in vitro. The leader sequence fragment typically encodes a signal peptide comprised of hydrophobic amino acids which direct the secretion of the protein from the cell.

DNA encoding suitable signal sequences can be derived from genes for secreted yeast proteins, such as the yeast invertase gene [E.P.O. Pub. No. 12873; J.P.O. Pub. No.

62,096,086] and the A-factor gene [U.S. Pat. No. 4,588, 684]. Alternatively, leaders of non-yeast origin, such as an interferon leader, exist that also provide for secretion in yeast [E.P.O. Pub. No. 600573].

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (typically about 25 to about 50 amino acid residues) [U.S. Pat. Nos. 4,546,083 and 4,870,008; and E.P.O. Pub. No. 324274]. Additional leaders employing an alpha-factor leader fragment that provides for secretion include hybrid alpha-factor leaders made with a presequence of a first yeast, but a pro-region from a second yeast alphafactor. See, e.g., P.C.T. WO 89/02463.

Typically, transcription termination sequences recognized by yeast are regulatory regions located 3' to the translation stop codon and thus, together with the promoter, flank the coding sequence. These sequences direct the transcription of an mRNA which can be translated into the polypeptide encoded by the DNA. Examples of transcription terminator sequence and other yeast-recognized termination sequences, such as those coding for glycolytic enzymes, are known to those of skill in the art.

Typically, the above described components, comprising a promoter, leader (if desired), coding sequence of interest, and transcription termination sequence, are put together into expression constructs. Expression constructs or cassettes are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 [Botstein et al., *Gene*, 8:17–24 (1979)], pCl/1 [Brake et al., *Proc. Natl. Acad. Sci USA*, 81:4642–4646 (1984)], and YRp17 [Stinchcomb et al., *J. Mol. Biol.*, 158:157 (1982)]. In addition, a replicon may be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Enter a high or low copy number vector may be selected, depending upon the effect on the host of the vector and the PACE polypeptides. See e.g., Brake et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al., *Methods in Enzymol.*, 101:228–245 (1983)]. An integrating vector may be directed to a specific locus in yeast by selecting the appropriate homologous sequence for inclusion in the vector. See Orr-Weaver et al., supra. One or more expression constructs may integrate, possibly affecting levels of recombinant protein produced [Rine et al., *Proc. Natl. Acad. Sci. USA*, 80:6750 (1983)]. The chromosomal sequences included in the vector can occur either as a single segment in the vector, which results in the integration of the entire vector, or as two segments homologous to adjacent segments in the chromosome and flanking the expression construct in the vector, which results in the stable integration of only the expression construct.

Typically, extrachromosomal and integrating expression vectors may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al., *Microbiol. Rev.*, 51:351 (1987)].

Alternatively, some of the above described components can be put together into transformation vectors. Transformation vectors are typically made up of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: Candida albicans [Kurtz, et al., *Mol. Cell. Biol.*, 6:142 (1986)], Candida maltosa [Kunze et al., *J. Basic Microbiol.*, 25:141 (1985)]; Hansenula polymorpha [Gleeson et al., *J. Gen. Microbiol.* 132:3459 (1986); Roggenkamp et al., *Mol. Gen. Genet.* 202:302 (1986)]; Kluyveromyces fragilis [Das et al., *J. Bacteriol.* 158:1165 (1984)]; Kluyveromyces lactis [De Louvencourt et al., *J. Bacteriol.* 154:737 (1983); Van den Berg et al., *Bio/Technology* 8:135 (1990)]; Pichia guillerimondii [Kunze et al., *J. Basic Microbiol.* 25:141 (1985)]; Pichia pastoris [Cregg et al., *Mol. Cell. Biol.* 5:3376 (1985); U.S. Pat. Nos. 4,837,148 and 4,929,555]; Saccharomyces cerevisiae [Hinnen et al., *Proc. Natl. Acad. Sci. USA* 75:1929 (1978); Ito et al., *J. Bacteriol.* 153:163 (1983)]; Schizosaccharomyces pombe [Beach and Nurse, *Nature* 300:706 (1981)]; and Yarrowia lipolytica [Davidow, et al., *Curr. Genet.* 10:380471 (1985); and Gaillardin et al., *Curr. Genet.* 10:49 (1985)].

Methods of introducing exogenous DNA into yeast hosts are well-known in the art, and typically include either the transformation of spheroplasts or of intact yeast cells treated with alkali cations. Transformation procedures usually vary with the yeast species to be transformed. See e.g., Kurtz et al., *Mol. Cell. Biol.* 6:142 (1986); Kunze et al., *J. Basic Microbiol.* 25:141 (1985) for Candida. See, e.g., Gleeson et al., *J. Gen. Microbiol.* 132:3459 (1986); Roggenkamp et al., *Mol. Gen. Genet.* 202:302 (1986) for Hansenula. See, e.g., Das et al., *J. Bacteriol.* 158:1165 (1984); De Louvencourt et al., *J. Bacteriol.* 154:1165 (1983); Van den Berg et al., *Bio/Technology* 8:135 (1990) for Kluyveromyces. See, e.g., Cregg et al., *Mol. Cell. Biol.* 5:3376 (1985); Kunze et al., *J. Basic Microbiol.* 25:141 (1985); U.S. Pat. Nos. 4,837,148 and 4,929,555 for Pichia. See, e.g., Hinnen et al., *Proc. Natl. Acad. Sci. USA* 75:1929 (1978); Ito et al., *J. Bacteriol.* 153:163 (1983) for Saccharomyces. See, e.g., Beach and Nurse, *Nature* 300:706 (1981) for Schizosaccharomyces. See, e.g., Davidow et al., *Curr. Genet.* 10:39 (1985); Gaillardin et al., *Curr. Genet.* 10:49 (1985) for Yarrowia.

Additionally, the PACE gene or a fragment thereof can be expressed in a bacterial system. Therein, a bacterial promoter is any DNA sequence capable of binding bacterial RNA polymerase and initiating the downstream (3") transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* [Raibaud et al., *Annu. Rev. Genet.* 18:173 (1984)]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., *Nature* 198:1056 (1987)], and maltose. Additional examples include promoter sequences derived from biosynthetic enzymes such as tryptophan (trp) [Goeddel et al., *Nuc. Acids Res.* 8:4057 (1980); Yelverton et al., *Nucl. Acids Res.* 9:731 (1981); U.S. Pat. No. 4,738,921; E.P.O. Pub. Nos. 36,776 and 121,775]. The β-lactomase (bla) promoter system [Weissmann, "The Cloning of Interferon and Other Mistakes" in *Interferon* 3 (ed. I. Gresser, 1981)]; bacteriophage lambda PL [Shimatake et al., *Nature* 292:128 (1981)]and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551, 433]. For example, the tac promoter is a hybrid trp-lac promoter comprised of both trp promoter and lac operon sequences that is regulated by the lac repressor [Amann et al., *Gene* 25:167 (1983); de Boer et al., *Proc. Natl. Acad. Sci.* 80:21 (1983)]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., *J. Mol. Biol.* 189:113 (1986); Tabor et al., *Proc Natl. Acad. Sci.* 82:1074 (1985)]. In addition, a hybrid promoter can also be comprised of a bacteriophage promoter and an *E. coli* operator region [E.P.O. Pub. No. 267,851].

In addition to a functioning promoter sequence, an efficient ribosome binding site is also useful for the expression of the PACE gene or fragment thereof in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon [Shine et al., *Nature* 254:34 (1975)]. The SD sequence is thought to promote binding of mRNA to the ribosome by the pairing of bases between the SD sequence and the 3' and of *E. coli* 16S rRNA [Steitz et al., "Genetic signals and nucleotide sequences in messenger RNA" in *Biological Regulation and Development: Gene Expression* (ed. R. F. Goldberger, 1979)]. To express eukaryotic genes and prokaryotic genes with weak ribosome-binding site [Sambrook et al., "Expression of cloned genes in *Escherichia coli*" in *Molecular Cloning: A Laboratory Manual*, cited above].

PACE may be expressed intracellularly. A promoter sequence may be directly linked with the PACE gene or a fragment thereof, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase [E.P.O. Pub. No. 219,237].

Fusion proteins provide an alternative to direct expression. Typically, a DNA sequence encoding the N-terminal portion of an endogenous bacterial protein, or other stable protein, is fused to the 5' end of heterologous PACE coding sequences. Upon expression, this construct will provide a fusion of the two amino acid sequences. For example, the bacteriophage lambda cell gene can be linked at the 5' terminus of the PACE gene or fragment thereof and expressed in bacteria. The resulting fusion protein preferably retains a site for a processing enzyme (factor Xa) to cleave the bacteriophage protein from the PACE gene or fragment thereof [Nagai et al., *Nature* 309:810 (1984)].

Fusion proteins can also be made with sequences from the lacZ [Jia et al., *Gene* 60:197 (1987)], trpE [Allen et al., *J. Biotechnol.*, 5.93 (1987); Makoff et al., *J. Gen. Microbiol.* 135:11 (1989), and Chey [E.P.O. Pub. No. 324,647]genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the PACE polypeptide. Through this method, mature PACE polypeptides can be isolated [Miller et al., *Bio/Technology*, 7:698 (1989)].

Alternatively, PACE polypeptides can also be secreted from the cell by creating chimeric DNA molecules that encode a fusion protein comprised of a signal peptide sequence fragment that provides for secretion of the PACE polypeptides in bacteria [U.S. Pat. No. 4,336,336]. The signal sequence fragment typically encodes a signal peptide comprised of hydrophobic amino acids which direct the secretion of the protein from the cell. The protein is either secreted into the growth media (Gram-positive bacteria) or into the periplasmic space, located between the inner and outer membrane of the cell (gram-negative bacteria). Preferably there are processing sites, which can be cleaved either in vivo or in vitro, encoded between the signal peptide fragment and the PACE polypeptide.

DNA encoding suitable signal sequences can be derived from genes for secreted bacterial proteins, such as the *E. coli* outer membrane protein gene (ompA) [Masui et al., in *Experimental Manipulation of Gene Expression* (1983); Ghrayeb et al., *EMBO J.* 3:2437 (1984)] and the *E. coli* alkaline phosphatase signal sequence (phoA) [Oka et al., *Proc. Natl. Acad. Sci.* 82:7212 (1985)]. As an additional example, the signal sequence of the alpha-amylase gene from various Bacillus strains can be used to secrete heterologous proteins from *B. subtilis* [Palva et al., *Proc. Natl. Acad. Sci. USA* 79:5582 (1982); E.P.O. Pub. No. 244,042].

Typically, transcription termination sequences recognized by bacteria are regulatory regions located 3' to the translation stop codon and thus, together with the promoter, flank the coding sequence. These sequences direct the transcription of an mRNA which can be translated into the polypeptide encoded by the DNA. Transcription termination sequences frequently include DNA sequences (of about 50 nucleotides) which are capable of forming stem loop structures that aid in terminating transcription. Examples include transcription termination sequences derived from genes with strong promoters, such as the trp gene in *E. coli* as well as other biosynthetic genes.

Typically, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The description of similar replicon systems, including copy number parameters are described in detail above in connection with yeast expression systems. Such description is also applicable to bacterial systems.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome [E.P.O. Pub. No. 127, 328]. Integrating vectors may also be comprised of bacteriophage or transposon sequences.

Typically, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al., *Annu. Rev. Microbiol.* 32:469 (1978)]. Selectable markers may also include biosynthetic genes, such as those in the histidine, tryptophan, and leucine biosynthetic pathways.

Alternatively, some of the above described components can be put together in transformation vectors. Transformation vectors are typically comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for the following bacteria: *Bacillus subtilis* [Palva et al., *Proc. Natl. Acad. Sci. USA* 79:5582 (1982); E.P.O. Pub. Nos. 36,259 and 63,953; P.C.T. WO 84/04541]; *E. coli* [Shimatake et al., *Nature*, 292:128 (1981); Amann et al., *Gene*, 40:183 (1985); Studier et al., *J. Mol. Biol.* 189:113 (1986); E.P.O. Pub. Nos. 36,776, 136,829 and 136,907; U.K. Patent Application Ser. No. 8418273]; *Streptococcus cremoris* [Powell et al., *Appl. Environ. Microbiol.* 54:655 (1988)]; *Streptococcus lividans* [Powell et al., *Appl. Environ. Microbiol.* 54:655 (1988)]; *Streptomyces lividans* [U.S. Pat. No. 4,745,056].

Methods of introducing exogenous DNA into bacterial hosts are well-known in the art, and typically include either the transformation of bacteria treated with CaCl$_2$ or other agents, such as divalent cations and DMSO. DNA can also be introduced into bacterial cells by electroporation. Transformation procedures usually vary with the bacterial species to be transformed. See e.g., [Masson et al., *FEMS Microbiol. Lett.* 60:273 (1989); Palva et al., *Proc. Natl. Acad. Sci. USA* 79:5582 (1982); E.P.O. Pub. Nos. 36,259 and 63,953; P.C.T. WO 84/04541, Bacillus], [Miller et al., *Proc. Natl. Acad. Sci.* 85:856 (1988); Wang et al., *J. Bacteriol.* 172:949 (1990) for Campylobacter]; [Cohen et al., *Proc. Natl. Acad. Sci.* 69:2110 (1973); Dower et al., *Nucleic Acids Res.* 16:6127 (1988); Kushner, "An improved method for transformation of *Escherichia coli* with ColE1-derived plasmids" in *Genetic Engineering: Proceedings of the International Symposium on Genetic Engineering* (eds. H. W. Boyer and S. Nicosia, 1978); Mandel et al., *J. Mol. Biol.* 53:159 (1970); Taketo, *Biochim. Biophys. Acta* 949:318 (1988) for Escherichia], [Chassy et al., *FEMS Microbiol. Lett.* 44:173 (1987) for Lactobacillus]; [Fiedler et al., *Anal. Biochem* 170:38 (1988) for Pseudomonas]; [Augustin et al., *FEMS Microbiol. Lett.* 66:203 (1990) for Staphylococcus]; [Barany et al., *J. Bacteriol.* 144:698 (1980); Harlander, "Transformation of Streptococcus lactis by electroporation," in *Streptococcal Genetics* (ed J. Ferretti and R. Curtiss III, 1987); Perry et al., *Infec. Immun.* 32:1295 (1981); Powell et al., *Appl. Environ. Microbiol.* 54:655 (1988); Somkuti et al., *Proc. 4th Evr. Cong. Biotechnology* 1:412 (1987) for Streptococcus].

C. Expression in Insect Cells

In one aspect of the invention, enhanced processing of a precursor polypeptide to a mature polypeptide is achieved by introducing into an insect host cell DNA sequences coding for PACE, yielding a recombinant insect cell. The precursor polypeptide and PACE are related in that the precursor has at least one selectively cleavable peptide bond, which is cleavable by PACE. The transcriptional initiation and expression of PACE allows for an enhanced production of PACE as compared to the unmodified host.

The polynucleotide encoding PACE is inserted into a suitable insect expression vector, and is operably linked to the control elements within that vector. Vector construction employs techniques which are known in the art. Various constructs can be prepared once the desired PACE DNA sequence is obtained.

Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector, which allows for the homologous recombination of the heterologous gene into the baculovirus genome, and appropriate insect host cells and growth media.

After inserting the PACE DNA sequence into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin No. 1555* (1987) (hereinafter "Summers and Smith"), and incorporated by reference.

Prior to inserting the PACE DNA sequence into the baculovirus genome, the above described components, comprising a promoter, leader (if desired), coding sequence of interest, and transcription termination sequence, are typically assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT [see, e.g., Luckow and Summers, *Virology,* 17:31 (1989)].

The plasmid usually also contains the polyhedrin polyadenylation signal [Miller et al., *Ann. Rev. Microbiol.,* 42:177 (1988) and a prokaryotic ampicillin-resistance (amp) gene and origin of replication for selection and propagation in *E. coli.*

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein [Friesen et al., "The Regulation of Baculovirus Gene Expression," in *The Molecular Biology of Baculoviruses* (ed. Walter Doerfler, 1986); E.P.O. Pub. Nos. 127,839 and 155,476]; and the gene encoding the p10 protein [Vlak et al., *J. Gen. Virol.* 69:765 (1988)].

DNA encoding suitable signal sequences can be derived from genes for secreted insect or baculovirus proteins, such as the baculovirus polyhedrin gene [Carbonell et al., *Gene,* 73:409 (1988)]. Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon [Maeda et al., *Nature* 315:592 (1985)]; human gastrin-releasing peptide [Lebacq-Verheyden et al., *Molec. Cell. Biol.* 8:3129 (1988)]; human IL-2 [Smith et al., *Proc. Nat'l Acad. Sci. USA,* 82:8404 (1985)]; mouse IL-3 [Miyajima et al., *Gene,* 58:273 (1987); and human glucocerebrosidase [Martin et al., *DNA,* 7:99 (1988)] can also be used to provide for secretion in insects.

In some instances, as described above, it may be desirable to have a plurality of copies, two or more, of the gene expressing the expression product precursor in relation to the PACE DNA sequence or vice versa. Some of the embodiments of the present invention include recombinant production of multiple proteins, for instance PACE and one or several heterologous precursor polypeptides. This may be accomplished by several different strategies. For example, PACE may be produced by expression of a gene encoding PACE in the baculovirus/insect cell expression system described herein. PACE so produced may then be used to cleave enzymatically a heterologous precursor polypeptide, thereby generating a more mature form of the protein. Of course, both PACE and the precursor polypeptide may be produced by independent baculovirus/insect cell expression systems and subsequently admixed.

Alternatively, PACE and one or more precursor polypeptides may be simultaneously produced by expression of the corresponding genes in the same insect cell. Each gene may be introduced into the insect cell by a separate transformation event, for instance separate transfections, transfection and baculovirus infection, or multiple baculovirus infections. Various combinations will be apparent to those skilled in the art. Transfer vectors can also be constructed which have two or more sets of operably linked expression regulating elements described above. Each set of expression elements has a unique restriction site into which a different gene may be inserted. Each set of elements may use the same type of promoter, or a different promoter may be used for each set. The enzyme/substrate ratio of PACE and precursor polypeptides may be optimized by use of different promoters with varying relative efficiencies.

Finally, a transfer vector incorporating multiple genes encoding PACE and one or more precursor polypeptides may be designed such that all genes are expressed as a polycistronic message under the control of a single set of regulatory elements. The resulting polyprotein can be processed into component parts by the autocatalytic activity of the PACE moiety, or by the incorporation of recognition sites for a site specific endopeptidase, such as signal peptidase, between functional domains.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the heterologous protein from insect cells. The leader sequence fragment typically encodes a signal peptide comprised of hydrophobic amino acids which direct the translocation of the protein into the endoplasmic reticulum.

After insertion of the PACE DNA sequence and/or the gene encoding the expression product precursor, an insect cell host is co-transformed with the heterologous DNA of the transfer vector and the genomic DNA of wild type baculovirus—usually by co-transfection. The promoter and transcription termination sequence of the construct will typically comprise a 2–5 kb section of the baculovirus genome. Methods for introducing heterologous DNA into the desired site in the baculovirus virus are known in the art [see, e.g., Summers and Smith, cited above; Ju et al. (1987) cited above; Smith et al., *Mol. Cell. Biol.,* 3:2156 (1983);

and Luckow and Summers (1989) cited above]. For example, the insertion can be into a gene such as the polyhedrin gene, by homologous double crossover recombination; insertion can also be into a restriction enzyme site engineered into the desired baculovirus gene [Miller et al., *Bioessays*, 4:91 (1989)]. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. The beauty of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 µm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies ["Current Protocols in Microbiology", Vol. 2 (Ausubel et al. eds) at 16.8 (Supp. 10, 1990); Summers and Smith, cited above; Miller et al. (1989), cited above].

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda*, and *Trichoplusia ni* [P.C.T. Pub. No. WO89/046699; Carbonell et al., *J. Virol.* 56:153 (1985); Wright, *Nature* 321:718 (1986); Smith et al., *Mol. Cell. Biol.* 3:2156 (1983); and see generally, Fraser et al., *In Vitro Cell. Dev. Biol.* 25:225 (1989)].

Cells and cell culture media are commercially available for both direct and fusion expression of heterologous polypeptides in a baculovirus/expression system. Cell culture technology is generally known to those skilled in the art [see, e.g., Summers and Smith, cited above].

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by known techniques, such as, chromatography (e.g., HPLC, affinity chromatography, ion exchange chromatography), electrophoresis, density gradient centrifugation, solvent extraction, or the like. As appropriate, the product may be further purified, as required, to remove substantially any insect proteins which are also secreted in the medium or result from lysis of insect cells, to provide a product which is at least substantially free of host debris, e.g., proteins, lipids and polysaccharides.

D. Deposit of biological material

*Escherichia coli* strain HB101 host cells transformed with a plasmid containing the PACE gene of FIG. 2, PACE/pBS24.1 have been deposited on Nov. 30, 1990, with the American Type Culture Collection (ATCC), Rockville, MD, and designated as PACE/pBS24.1 in *E. coli*. This deposit will be maintained under the terms of the Budapest Treaty on the International Recognition of the Deposit of Microorganisms for purposes of patent procedure. The accession number is ATCC 68486.

This deposit is provided merely as convenience to those of skill in the art, and is not an admission that a deposit is required under 35 U.S.C. §112. The nucleic acid sequence [SEQ ID NO: 3] of this plasmid, as well as the amino acid sequence [SEQ ID NO: 4] of the polypeptide encoded thereby, are incorporated herein by reference and are controlling in the event of any conflict with the description herein. A license may be required to make, use, or sell the deposited material, and no such license is hereby granted.

The following experimental section is intended to be merely illustrative and does not limit the present scope in any way. The following examples illustratively describe the construction of plasmids for the expression and production of PACE in mammalian cells, and the co-expression of PACE and the blood coagulation factor, Factor IX, in mammalian cells.

Example 1—Construction of PACE cDNA

This example demonstrates the construction of a composite recombinant cDNA which encodes mammalian PACE, and the characterization of the polypeptide encoded therein. The cDNA was constructed from two isolated cDNAs encoding separate portions of the PACE molecule.

The molecular cloning of cDNAs encoding PACE was accomplished as follows. An oriented cDNA library was constructed in the yeast expression vector pAB23BXN using poly(A)$^+$ mRNA isolated from the human liver cell line HEPG2. pAB23BXN is a derivative of pAB23BX [D. Schild et al., *Proc. Natl. Acad. Sci. U.S.A.*, 87:2916 (1990)] into which a synthetic polylinker, that contained Bst X1 and Not 1 sites, was inserted for unidirectional cDNA cloning. Oligonucleotide probes were used to isolate a 3,295 bp clone from the library. These probes were synthesized using the sequence of a partial cDNA clone (3.1 kb) which putatively encodes a portion of the fur gene product [A.J.M. Roebroek et al., *EMBO J.*, 5:2197 (1986)].

In order to isolate the 5'-end of the PACE cDNA, a second cDNA library from HEPG2 poly (A)$^+$ RNA mRNA was constructed in γZAPII [Stratagene], using specific internally primed message. Using the longest clone isolated from this library, a composite cDNA for PACE was constructed. The composite cDNA contains 4,351 bp and is comprised of 388 bp of 5'-untranslated region, a putative coding sequence corresponding to 794 amino acids, and 1597 bp of 3'-untranslated region, including two termination codons and a tail of 17 dA residues.

The full sequence of the composite PACE cDNA and the encoded protein sequence is shown in FIG. 2 [SEQ ID NO: 3] with the encoded protein sequence shown above that of the cDNA sequence. The numbering is based on the significant open reading frame (ORF) in the cDNA. Oligonucleotide adaptor sequences present in the cDNA are indicated by lower-case letters. The putative signal peptide is indicated by underlining and the transmembrane domain (TM) by shading. Likely active site residues are indicated by asterisks. Consensus sites for Asn-linked glycosylation are marked by diamonds and cysteine residues by bars. Potential dibasic proteolytic processing sites are indicated by arrows.

Based upon the composite PACE cDNA structure, the following is deduced. The translation of PACE is probably initiated at the ATG start codon at nucleotide #1. Although there are four ATG codons upstream from nucleotide #1, the ATG at nucleotide #1 is the only in-frame methionine codon in the 5'-region of the cDNA, and the subsequent 26 amino acids constitute a classical hydrophobic signal sequence, which is usually associated with a membrane-bound protein. The signal peptidase cleavage site occurs between amino acids #26–27.

A large ORF encodes a PACE precursor protein with a calculated molecular weight of 86.7 kD. In addition, several paired basic amino acid residues are located in the amino-terminal region of the PACE precursor (FIG. 2), and could represent proteolytic/autolytic processing sites. The coding sequence contains three consensus sites for N-linked glycosylation and twenty-two cysteine residues. The active site is in the ORF and includes a triad of amino acids: aspartic acid (Asp #153), histidine (His #194), and serine (Ser #368). A cysteine-rich region (CRR) is also present and, as shown in FIG. 2, is located in the vicinity of amino acid Cys #587 to amino acid Cys #675. A putative hydrophobic transmembrane domain (TM) is located downstream from the cysteine-rich region, at approximately amino acid Val #716 to amino acid Leu #738.

The 3'-untranslated region is relatively long (1597 bp) and contains a possible polyadenylation signal (ATTAAA) at nucleotides #3939–3943 of the composite clone. Of particular note are numerous regions of extensive potential secondary structure involving coding sequences, and the 3'-untranslated sequences around the termination codon.

Example 2—Plasmid Construction and Expression of PACE cDNA in Mammalian COS-1 Cells This example demonstrates the expression of recombinant PACE cDNA in COS-1 cells. The mammalian cell expression system was constructed as follows.

A truncated 2.47 kbp PACE cDNA fragment is employed, which was generated from the composite PACE cDNA by PCR. The method utilized synthetic primers which hybridized to the 5'-end of the PACE coding sequence and to approximately 70 bp into the 3'-untranslated region. The 5'primer generated an EcoRI site for cloning into pBluescript SK⁻ [Stratagene]. The 3primer generated a SalI cloning site. All of the PCR products were verified by the M13 dideoxy sequencing method.

The 2.47 kbp (EcoRI-SalI) PACE cDNA fragment from pBluescript-PACE included the 794 codon PACE coding sequence [SEQ ID NO: 1] (FIG. 1) and 74 bases of 3'-untranslated sequence before a SalI site [van den Ouweland et al, cited above]. At the 5'-end, using the EcoRI PCR primer, the sequence immediately preceding the ATG was modified to conform to the consensus translation start site.

The 2.47 kb truncated cDNA was inserted into the cloning site (EcoRI-SalI) of the SV40-based expression vector pMT3 to generate the plasmid pMT3-PACE. The pMT3 vector is a derivative of the vector pMT2 [R. J. Kaufman et al., *Mol. Cell. Biol.*, 9:946 (1989)] in which the DHFR coding region on the 3'-side of the cloning site has been removed. pMT3 has been deposited with the American Type Culture Collection (ATCC), Rockville, MD (USA) under Accession Number ATCC 40348. pMT3 can also be generated starting with pMT2-vWF, which is deposited at the ATCC under Accession Number ATCC #67122 [see PCT application PCT/US87/00033].

DNA of the resulting vector, pMT3-PACE, was purified and introduced for transient expression into SV40-transformed monkey kidney cells (COS-1) using a calcium phosphate transfection protocol as described in Chen, C. A., and Okayama, H., *BioTechniques*, 6:632–638 (1988); and C. Chen and H. Okayama, *Mol. Cell. Biol.* 7:745 (1987). Cells were transfected with 40 μg of plasmid per 10 cm dish in 10 mls of medium or, in the case of co-transfections, an equimolar ratio of plasmids totalling 60 μg per 10 cm dish in 10 ml of medium.

To monitor PACE synthesis, pMT3-PACE transfected COS-1 cells were radiolabeled 48–60 hours following transfection using S-labeled amino acids, e.g., $^{35}$S-Met and $^{35}$S-Cys, in medium lacking those amino acids, e.g., Cys and Met. Untransfected cells were similarly treated. After a 30 minute pulse period, cell extracts were prepared by lysis in NP-40 lysis buffer [A. J. Dorner and R. J. Kaufman (1990), *Meth. Enzymol.*, 185:577 (1990)] or were chased by removing the labeling medium and replacing it with complete medium for additional incubation. Cell extracts and conditioned medium were treated with protease inhibitors and immunoprecipitated using the method described in Wise et al, *Cell*, 52:229–236 (1988).

Immunoprecipitates were performed with rabbit anti-PACE antiserum produced against a PACE-*E. coli* fusion protein. Rabbit anti-PACE antiserum was generated against the catalytic domain of PACE by expression of amino acids 146 to 372 of PACE as a human superoxide dismutase (SOD) fusion protein in *E. coli*. The DNA fragment for expression was generated by polymerase chain reaction (PCR) and cloned into the superoxide dismutase (SOD) fusion vector pTAC7 [Steimer et al, *J. Virol.*, 58:9 (1986)]. The induced fusion protein was purified by preparative polyacrylamide gel electrophoresis, eluted and used to immunize rabbits in complete Freunds adjuvant.

The immunoprecipitated samples were then analyzed by SDS-polyacrylamide gel electrophoresis [SDS-PAGE; (A 8%; B,C 6% acrylamide)]. The gels were prepared for fluorography in EnHance [Dupont].

In the lysates from the control COS-1 cells which were not transfected with pMT3-PACE, immunoreactive proteins with anti-PACE antiserum were not detected. However, in extracts from pMT3-PACE transfected cells, immunoreactive species were detected that migrated in the gels primarily as a doublet of approximately 90 kD. These PACE immunoprecipitates were treated with the endoglycosidase enzyme, N-glycanase [Genzyme], using the method described in A. J. Dorner and R. J. Kaufman (1990), cited above. This treatment resulted in a shift in the electrophoretic mobility of the labeled proteins in the gels which was consistent with the presence of asparagine-linked oligosaccharides. However, these digestions did not fully reduce the complexity of the bands, suggesting that differential glycosylation may not be the source of the observed heterogeneity in the expressed PACE.

In order to analyze secretion of PACE, the $^{35}$S-labeled cells were incubated for a 12 hour chase period in a medium containing an excess of unlabeled amino acids. The secreted products from the conditioned medium and in cell lysates were immunoprecipitated with the anti-PACE antiserum. The medium from the pMT3-PACE transfected cells yielded an immunoreactive protein which migrated in the gels as a 75 kD polypeptide. The relative quantity of the 75 kD immunoprecipitated PACE polypeptide observed in the conditioned medium was 5 to 10 fold less than that detected in the cell lysate or remaining inside the cell at the 12 hour chase period.

This secreted PACE species, which differs in apparent size from the intracellular species, may represent a truncated molecule which is missing its transmembrane and/or intracellular domains. This difference in size may possibly be the result of auto-proteolysis at the paired arginine residues, #497–498, due to the large overproduction of PACE in the transfected COS-1 cells.

More extensive pulse-chase experiments demonstrated that the PACE translation product does not accumulate to high levels inside the cell compared to another integral membrane glycoprotein (influenza hemagglutinin) when synthesized at similar levels.

Example 3—Coexpression of PACE and vWF in Cos-1 Cells

This example demonstrates the effect of recombinant PACE expression on the processing of von Willebrand factor (vWF), a protein involved in blood coagulation, produced during co-expression of the two recombinant polypeptides in COS-1 cells.

vWF is a multimeric plasma protein which is normally synthesized in endothelial cells as a large precursor polypeptide (prepro-vWF). Upon translocation into the endoplasmic reticulum (ER), the precursor polypeptide undergoes signal peptide cleavage and N-linked oligosaccharide addition. In the ER, pro-vWF forms carboxy-terminal linked disulfide-bonded dimers that, upon transport to the Golgi and post-Golgi compartments, undergo a complex series of processing steps. These steps include: processing of N-linked carbohydrate, O-linked glycosylation, assembly of disulfide linked multimers, and propeptide cleavage [R. I. Handin and D. D. Wagner, in *Progress in Hemostasis and Thrombosis*, vol 9, B. S. Coller, Ed. (W. B. Saunders, Philadelphia, 1989) pp. 233–259].

In endothelial cells, vWF follows both a constitutive and regulated pathway of secretion. Transfection of a vWF cDNA expression vector into COS-1 cells directs the synthesis of prepro-vWF [D. T. Bonthron et al., *Nature*, 324:270 (1986)]. However, although COS-1 cells do possess a protease capable of recognizing and cleaving the vWF propeptide, this process is inefficient. Thus, approximately 50% of the secreted protein from a typical expression study is uncleaved pro-vWF [R. J. Wise et al., *Cell*, 52:229 (1988)]. If PACE recognizes and cleaves the vWF propeptide, then co-expression of PACE with Pro-vWF should result in greater conversion of pro-vWF to the mature form.

In order to demonstrate PACE conversion of pro-vWF to the mature form, COS-1 cells were transfected with either pMT3-PACE, pMT2-vWF [D. T. Bonrthron et al., *Nature*, 324:270 (1986)], or cotransfected with both plasmids. Cells were transfected with 40 µg of plasmid, or in the case of co-transfections with an equimolar ratio of plasmids totaling 60 µg per 10 cm dish in 10 ml of medium. The transfected cells were pulse-labeled with $^{35}$S-amino acids for 30 minutes and lysed, as described in Example 2, or were chased by removing the labeling medium and replacing it with complete medium for additional incubation.

Cell extracts and conditioned medium samples were treated with protease inhibitors and immunoprecipitated. Immunoprecipitation was with an anti-vWF polyclonal antibody [Dako Corp.] which specifically recognizes the mature portion of vWF. The same samples were also immunoprecipitated with a monoclonal antibody specific for the propeptide of vWF (anti-vWAgII).

Immunoprecipitation of cell extracts from 30 minute pulse-labeled cells with anti-VWF antibody detected only single chain pro-vWF precursor in COS-1 cells transfected with pMT2-vWF alone. The conditioned medium yielded both cleaved (mature) and uncleaved (pro-vWF) forms in nearly equal amounts.

In contrast, in cellular extracts of COS-1 cells that were co-transfected with pMT2-vWF and pMT3-PACE, the 100 kD propeptide and 225 kD mature subunit were detected at the 30 minute pulse time point. This indicates that there was a significant amount of propeptide cleavage at this time point. In the conditioned medium, following a 12 hour chase period, the secreted vWF was completely processed to the 225 kD mature protein. Analysis of the amino-terminus of $^{35}$S-Met labeled 225 kD product by 21 cycles of automated Edman degradation, followed by scintillation counting, yielded results which were consistent with cleavage at the correct site within the vWF precursor.

Cleavage of pro-vWF to the mature form of vWF also yields the vWF propeptide. The production of this propeptide in the above studies was also monitored. The presence of this propeptide was shown by immunoprecipitation with a monoclonal antibody directed against the propeptide, also known as vWF Antigen II [P.J. Fay et al., *Nature*, 232:995 (1986)]. Analysis of the immunoprecipitated products was by polyacrylamide gel electrophoresis, as described above.

The results showed that immunoprecipitates from extracts of cells transfected with pMT2-vWF alone yielded unprocessed pro-vWF (due to the presence of the uncleaved propeptide in the precursor molecule). Immunoprecipitates of extracts from cells co-transfected with pMT2-vWF and pMT3-PACE yielded the vWF propeptide, which migrated in the gels as a doublet at 100 kD. The doublet was reduced to a single species after digestion with N-glycanase, indicating that the apparent difference in molecular weights was due to differential glycosylation.

Using a similar analysis, the conditioned cell media were also analyzed for the presence of propeptide. Immunoprecipitates of the conditioned medium of the pMT2-vWF transfected cells yielded the free propeptide and multimers of vWF. The multimers contained a mixture of mature vWF and pro-vWF, indicating incomplete processing in the singly transfected COS-1 cells. However, the anti-AgII antibody immuno-precipitates from the conditioned medium from co-transfected cells yielded only free propeptide, indicating that the pro-vWF had been totally converted into the mature form.

In these studies with the detection of the propeptide, formation of vWF multimers in the media from singly transfected and co-transfected cells was confirmed by non-reducing agarose gel electrophoresis, using essentially the technique described by R. J. Wise et al., *Cell*, 52:229 (1988). The agarose gel electrophoresis analysis indicated that the amount of vWF multimers in the media from the singly and co-transformed cells was comparable.

Example 4—Substrate Specificity of PACE

In order to test the recognition specificity of the recombinant PACE for substrates with a Lys-Arg or Lys-Lys cleavage site, studies were performed with mutants in the cleavage site of pro-vWF. One of the mutants, designated vWF DES, contained a non-conservative substitution, Lys- Arg-Ser (KRS) to Asp-Glu-Ser (DES), at the propeptide cleavage site. The other mutant, designated vWF KKS, contained a conservative substitution of Lys-Lys-Ser for Lys-Arg-Ser at the propeptide cleavage site.

Plasmids containing the mutant vWF genes were co-transfected with pMT3-PACE to determine the susceptibility of their expression products to cleavage with PACE. The analysis was carried out as described in Example 3 above.

The results of the analysis showed that when COS-1 cells were transfected with the plasmid encoding vWF DES, the labeled product was secreted as an uncleaved pro-vWF species. The same results were obtained with COS-1 cells which were co-transformed with both the vWF DES plasmid and with pMT3-PACE. When the expression products of COS-1 cells transfected with the plasmid encoding vWF KKS were examined, the labeled product was again secreted as an uncleaved pro-vWF species. When the expression products of the co-transformants which expressed both PACE and the KKS mutant protein were examined, although some of the secreted vWF remained uncleaved, a significant amount of propeptide cleavage had occurred.

The results of these studies with the mutated vWF sequences indicates that a non-conservative substitution at the natural Lys-Arg cleavage site of pro-vWF prevents cleavage by co-expressed recombinant PACE. However, a conservative substitution of Lys-Lys for Lys-Arg still allows an acceptable substrate for the recombinant protease.

Example 5—Expression of PACE in CHO Cells

This example illustrates the transformation of Chinese hamster ovary (CHO) cells with the PACE coding sequence. Suitable vectors were constructed as follows. pMT3-PACE was digested with SalI to linearize at the 3' end of PACE cDNA. The SalI site was filled-in with dNTPs and Klenow. The EcoRI linker was ligated to a blunt end and then digested with EcoRI. PACE cDNA was isolated on a gel and then ligated to EcoRI-linearized pMT2-EMC-DHFR. This latter plasmid is a minor derivative of pED4, described in R. Kaufman et al, *Nucl. Acids Res.*, 19(16):4485–4490 (1991).

Transformed DH5α colonies were picked for plasmid miniprep. Insert orientation was determined with KpnI, BamHI, BglII. The properly oriented clone was grown for large-scale plasmid preparation. The remainder of the miniprep DNA was used to transfect two CHO cell lines.

A lipofection kit [BRL] was used to transfect CHO cells on 60 mm culture dishes in OptiMEM medium. The two starting cell lines were CHO-DUKX and PM5F-0.1, which is a VWF-producing line derived from PM5F by selection for resistance of 0.1 μM DCF.

α-selection was started after splitting the cells to 100 mm plates. The CHO-DUKX line was selected in α-MEM/10% dialysed fetal calf serum (FCS). The PM5F line was selected in α-MEM-AAU/10% dialysed FCS. Both lines showed good growth during 3 days of α-medium selection. These α-selected cells were split. One plate of each line (called PACE-DUKX-α and PM5F-PACE-α) was passaged in α-medium for 10 days then frozen for storage.

Methotrexate (MTX) was added (0.05 μM) to the selection medium four days later. Many colonies formed over approximately 1 week. These colonies were pooled and split for selection in methotrexate at 0.1 μM about a week later. Again, many colonies formed which were pooled, split and continued in selection medium with 0.1 μM methotrexate. These amplified pools were then frozen for storage.

PM5F-PACE ("pool A") cells were pulse-labeled. Two subconfluent 100 mm plates were rinsed in serum-free medium. 1 ml of Cys/Met deficient medium supplemented with 250 μCi each of 35-S Met and 35-S Cys was added for a 15 minute pulse. One plate was lysed for immunoprecipitation of cell extract. Medium was removed from the other plate and 2 ml complete medium (serum-free) added for a 12 hour chase. At 12 hours, conditioned medium was collected and cells were lysed for immunoprecipitation. Cell lysis was in 1 ml of cold 0.5% Triton-X-100, M NaCl, 10 Mm Tris-HCl (pH 7.5), 5 Mm Na2-EDTA. Protease inhibitors were added to conditioned medium and cell extract. Immunoprecipitates of 0.5 ml of cell extract and 1 ml conditioned medium were performed with an anti-vWF antibody [DAKO] coupled two Affi-Gel and an anti-PACE antiserum [Chiron] secondarily bound to protein-A sepharose.

Precipitates were washed in cold lysis buffer and analysed on SDS-PAGE. Results were similar to that seen in PACE plus vWF COS-1 co-transfection experiments. With anti-PACE, a 95–100 kDA doublet band was precipitated in the 15 minute cell extract. At 12 hours, the intensity of this cell extract band was reduced approximately 10 fold. In the conditioned medium, at 12 hours, a 75–80 kDa single band was detected. With the anti-vWF, it was determined that the secreted vWF at 12 hours was completely processed mature vWF. In the cell extract samples, both pro-vWF and cleaved vWF were present.

These findings differ from that observed in the parent cell line, PM5F, in that secreted vWF is only partially processed and intracellular cleavage is minimal. For PM5F-PACE, a comparison of the autoradiographic intensities of the PACE bands and the vWF bands indicated that the level PACE expression is roughly ½ that of vWF.

The PACE-DUKX ("pool 4/4") was tested in the manner described above. The SDS-PAGE results from anti-PACE immunoprecipitates demonstrated an intracellular 95–100 kDa doublet band in pulsed (30 minute) cell extract and the apparent secretion of a smaller (75–80 kDa) immunoreactive species in the chased (18 hour) conditioned medium. In addition, in this labeling experiment, PM5F-PACE cells were analyzed for comparison. The intensities of the PACE bands in the 30 minute cell extract immunoprecipitates were equal for both cell lines.

Example 6—Co-Expression of PACE and Factor IX in CHO Cells

A CHO cell line producing recombinant Factor IX (IC4) [the IC4 cell line is described in Kaufman et al, *J. Biol. Chem.*, 261:9622–9628 (1986)] and Factor IX sequences were transfected with the PACE cDNA described above in Example 1 operably linked to another amplifiable marker, adenosine deaminase. The vector MT3SV2Ada [R. J. Kaufman et al, *Meth. Enzym.*, 185:537–566 (1990)] was chosen for PACE expression because it contains a selectable ADA transcription unit but no DHFR sequences and the PACE fragment could easily be inserted after digestion of the vector with EcoR1 and Sal1.

A vector fragment was isolated from low melt agarose, ligated in a ratio of 5:1 (fragment to vector), diluted in 10 mM Tris-HCl, pH 7.5, 1 mM EDTA, and used to transform DH5 bacteria [Dr. Douglas Hanahan, Cold Spring Harbor, N.Y.]. A nick-translated, $^{32}$P labelled PACE fragment was prepared and used for filter hybridization to screen transformed colonies.

Positively hybridizing colonies were isolated and DNA prepared for digestion with EcoR1 and Sal1 for confirmation of PACE insertion and with Bgl II for correct orientation of the fragment with respect to adenovirus major late promoter in the vector.

DNA from one colony was isolated for electroporation into the Factor IX producing cells, IC4. Pools of colonies have been selected for amplification by growth in 1.0 μM 2'-deoxycoformycin (DCF). The presence of PACE in these amplified lines was confirmed by $^{35}$S-methionine labelling and immunoprecipitation.

Biological activity of the Factor IX protein in the PACE/IX pools was analyzed by clotting assay, performed as described in Kaufman et al, *J. Biol. Chem.*, 261:9622–9628 (1986). Cells were plated in p60 tissue culture dishes. The next day medium was reduced (1.5 ml) and changed to α "defined" +1 μg/ml Vitamin K3.

The PACE/Factor IX pools were found to secrete between 2.0 and 3.1 fold more Factor IX biological activity than the original IC4 cell line. The results of a radioimmunoassay indicated increased levels of γ-carboxylated protein. These results are illustrated in Table I below.

TABLE I

| | Factor IX Assays in Original IC4 and PACE co-expressing Cell Lines | | | | |
|---|---|---|---|---|---|
| | CLOTTING | CLOTTING | | RIA | |
| Cell | ASSAY U/ml (pg/cell) | ASSAY U/ml (pg/cell) | GLA μg/ml | TOTAL μg/ml (pg/cell) | GLA TOTAL |
| IC4 | .28 (.32) | .18 (.18) | .1 | 20 (30) | .5% |
| | | Co-expressors | | | |
| | 0.1 μM DCF | 1.0 μM DCF | | 5 μM DCF | |
| A | .72 (.89) 2.7× | .45 (.48) 2.6× | .69 | 20 (29) | 3.4% |
| B | .53 (.76) 2.3× | .39 (.41) 2.3× | 1.05 | 22 (27) | 4.8% |
| C | .66 (.73) 2.2× | .35 (.41) 2.3× | .17 | 19 (54) | .8% |
| D | .46 (.66) 2.0× | .55 (.55) 3.1× | 1.14 | 17 (24) | 6.7% |
| E | .67 (.80) 2.5× | .49 (.52) 2.9× | .3 | 11 (34) | 2.7% |

From the first electroporation of MT3-PACE Ada into IC4 cells, cells were selected in a medium with 10% dialyzed fetal calf serum, penicillin, streptomycin, glutamine, 200 μM Methotrexate and Adenosine, alanosine, uridine and 0.1 μM DCF. Approximately 25 colonies were observed in plates that did not receive DNA.

A second electroporation performed was selected in the same manner and approximately 100 colonies were pooled into each of the 5 pools. Again, no colonies were observed on plates that did not receive DNA.

Expression of PACE was detected in each pool by 30 minute pulse with $^{35}$S Methionine followed by 2 hour chase and immunoprecipitation of cell extracts with α PACE antibody [Chiron Corporation, California]. In cells which express higher levels of PACE as a result of selection for further DCF resistance, secretion up to 10-fold greater levels of γ-carboxylated Factor IX was observed compared to the original IC4 cell line.

The coexpression of PACE did not produce any detectable change in the size of the Factor IX protein as monitored by immunoprecipitation with α FIX antibody [Hybridtech] and SDS gel electrophoresis.

Example 7—Baculovirus Expression of PACE

Two baculovirus expression cassettes were constructed for expression of PACE in insect cells. Cassette I was constructed using as the PCR template, PACE/pBS24.1, with primers fur 102 and fur 103:

102: 5'CCA CCT GTC TGA TCA ATG GAG CTG AGG CCC TGG TTG3'  [SEQ ID NO: 5]

103: 5'GAG GCC TGA TCA CTA CTC AGC CAG GTG TGA GGG CAT3'  [SEQ ID NO: 6].

The cassette was made without a transmembrane domain. The pCR product was extracted with phenol/chloroform and precipitated with ethanol. The PCR product was then cut with BclI and ligated to the pAC373 vector, which was cut with Bam HI and phosphatased. Cassette II was constructed using as the PCR template, PACE/pBS24.1, with primers fur 102 (above) and fur 104;

104: 5'GCA GCC TGA TCA CTA TGG AGG TAC GGG CAG CCC CTC3'  [SEQ ID NO: 7].

The pCR product was purified and cloned into pAC373 by the procedure described above for Construct I.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A transformed eukaryotic host cell comprising a recombinant polynucleotide sequence heterologous to said host cell encoding mammalian endopeptidase protein precursor processing enzyme, PACE, capable of cleaving precursor polypeptides at basic amino acid pairs, wherein said PACE encoding sequence is operably linked to an expression control sequence permitting expression of PACE by said cell; and a polynucleotide encoding a precursor polypeptide operably linked to a heterologous expression control sequence permitting expression of the precursor polypeptide encoded by the precursor polynucleotide, wherein said precursor polypeptide is a substrate for the encoded PACE and a precursor of a protein which requires gamma-carboxylation for biological activity, wherein the cell is capable of expressing the polynucleotides encoding PACE and the precursor polypeptide.

2. The host cell according to claim 1 wherein the encoded PACE and the precursor polypeptide, when expressed, are secreted.

3. The host cell according to claim 1 wherein said precursor polypeptide is a precursor polypeptide of a blood coagulation protein.

4. The host cell according to claim 3 wherein said blood coagulation protein is selected from the group consisting of Factor IX, Protein C, Protein S, Prothrombin Factor X, and Factor VII.

5. The host cell according to claim 4 wherein said blood coagulation protein is Factor IX.

6. The host cell according to claim 1 wherein said precursor polypeptide is a precursor polypeptide of bone-gamma carboxyglutamate protein.

7. The host cell according to claim 1, wherein said encoded PACE retains PACE biological activity and is selected from the group consisting of (a) SEQ ID NO: 2, (b) a soluble analog of SEQ ID NO: 2, and (c) an analog of SEQ ID NO: 2 encoded by a modified SEQ ID NO: 1 or SEQ ID NO: 3, which modification consists of 1 to 4 codon changes in a region of said encoding sequence not encompassing the active site of said PACE.

8. The host cell according to claim 1 wherein said recombinant polynucleotide is the cDNA sequence of SEQ ID No: 1 or SEQ ID No: 10.

9. The host cell according to claim 1 wherein said expression control sequence is heterologous to said host cell.

10. The host cell according to claim 1 wherein the host cell is selected from the group consisting of a mammalian cell, an insect cell, and a yeast cell.

11. The host cell according to claim 10, wherein the mammalian cell is a CHO cell.

12. A transformed eukaryotic host cell comprising a recombinant polynucleotide sequence heterologous to said host cell encoding mammalian endopeptidase protein precursor processing enzyme, PACE, capable of cleaving precursor polypeptides at basic amino acid pairs, wherein said PACE encoding sequence is operably linked to an expression control sequence permitting expression of PACE by said cell; and a polynucleotide encoding a precursor polypeptide operably linked to a heterologous expression control sequence permitting expression of the precursor polypeptide encoded by the precursor polynucleotide, wherein said precursor polypeptide is a substrate for the encoded PACE and a precursor of yon Willebrand Factor, wherein the cell is capable of expressing the polynucleotides encoding PACE and the precursor polypeptide.

13. The host cell according to claim 12 wherein the encoded PACE and the precursor polypeptide, when expressed, are secreted.

14. The host cell according to claim 12, wherein said encoded PACE retains PACE biological activity and is selected from the group consisting of (a) SEQ ID NO: 2, (b) a soluble analog of SEQ ID NO: 2, and (c) an analog of SEQ ID NO: 2 encoded by a modified SEQ ID NO: 1 or SEQ ID NO: 3, which modification consists of 1 to 4 codon changes in a region of said encoding sequence not encompassing the active site of said PACE.

15. The host cell according to claim 12 wherein said recombinant polynucleotide is the cDNA sequence of SEQ ID NO: 1 or SEQ ID NO: 3.

16. The host cell according to claim 12 wherein said expression control sequence is heterologous to said host cell.

17. The host cell according to claim 12 wherein the host cell is selected from the group consisting of a mammalian cell, an insect cell and a yeast cell.

18. The host cell according to claim 17, wherein the mammalian cell is a CHO cell.

19. A recombinant expression vector suitable for expression in a selected eukaryotic host cell comprising a polynucleotide sequence encoding mammalian endopeptidase protein precursor processing enzyme, PACE, capable of cleaving precursor polypeptides at basic amino acid pairs; and a polynucleotide sequence encoding a precursor polypeptide which requires gamma-carboxylation for biological activity and which is a substrate for PACE, operably linked to an expression control sequence permitting expression of the polynucleotide sequence in the eukaryotic host cell.

20. The vector according to claim 19 wherein said precursor polypeptide is a precursor polypeptide of bone-gamma carboxyglutamate protein.

21. The vector according to claim 19, wherein said encoded PACE retains PACE biological activity and is selected from the group consisting of (a) SEQ ID NO: 2, (b) a soluble analog of SEQ ID NO: 2, and (c) an analog of SEQ ID NO: 2 encoded by a modified SEQ ID NO: 1 or SEQ ID NO: 3, which modification consists of 1 to 4 codon changes in a region of said encoding sequence not encompassing the active site of said PACE.

22. The vector according to claim 19 wherein said recombinant polynucleotide is the cDNA sequence of SEQ ID NO: 1 or SEQ ID NO: 3.

23. The vector according to claim 19 wherein said host cell is selected from the group consisting of a mammalian cell, an insect cell, and a yeast cell.

24. The vector according to claim 19, wherein the mammalian cell is a CHO cell.

25. A recombinant expression vector suitable for expression in a selected eukaryotic host cell comprising a polynucleotide sequence encoding mammalian endopeptidase protein precursor processing enzyme, PACE, capable of cleaving precursor polypeptides at basic amino acid pairs; and a polynucleotide sequence encoding a precursor polypeptide which is a precursor of a blood coagulation protein and which is a substrate for PACE, operably liked to an expression control sequence permitting expression of the polynucleotide sequence in the eukaryotic host cell.

26. The vector according to claim 25 wherein said blood coagulation protein is selected from the group consisting of Factor IX, Protein C, Protein S, Prothrombin Factor X, and Factor VII.

27. The vector according to claim 26 wherein said blood coagulation protein is Factor IX.

28. The vector according to claim 25 wherein said precursor polypeptide is a precursor of von Willebrand Factor.

29. The vector according to claim 25 wherein the encoded PACE retains PACE biological activity and is selected from the group consisting of

SEQ ID NO: 2

(b) a soluble analog of SEQ ID NO: 2; and (c) an analog of SEQ ID NO: 2 encoded by a modified SEQ ID NO: 1 or SEQ ID NO: 3, which modification consists of 1 to 4 codon changes in a region of said encoding sequence not encompassing the active site of said PACE.

30. The vector according to claim 25 wherein the recombinant polynucleotide is the cDNA sequence of SEQ ID NO: 1 or SEQ ID NO: 3.

31. The vector according to claim 25 wherein said host cell is selected from the group consisting of a mammalian cell, an insect cell and a yeast cell.

32. The vector according to claim 31, wherein said mammalian cell is a CHO cell.

33. A method for producing a desired mature polypeptide and allowing the cleavage of a heterologous precursor polypeptide by the expressed recombinant PACE comprising culturing a transformed eukaryotic host cell comprising a heterologous polynucleotide encoding mammalian endopeptidase protein precursor processing enzyme, PACE, capable of cleaving precursor polypeptides at basic amino acid pairs, and a polynucleotide encoding a precursor polypeptide, wherein the precursor polypeptide is a substrate for the encoded PACE and requires gamma-carboxylation for biological activity, under conditions that allow expression of both recombinant PACE and the precursor polypeptide.

34. The method according to claim 33 wherein said PACE retains PACE biological activity and is selected from the group consisting of (a) SEQ ID NO: 2, (b) a soluble analog of SEQ ID NO: 2, and (c) an analog of SEQ ID NO: 2 encoded by a modified SEQ ID NO: 1 or SEQ ID NO: 3, which modification consists of 1 to 4 codon changes in a region of said encoding sequence not encompassing the active site of said PACE.

35. The method according to claim 34 wherein said conditions permit the secretion of both recombinant soluble PACE and said precursor polypeptide.

36. A method of increasing the yield of a selected biologically active protein having a precursor which is a substrate for PACE comprising culturing a transformed mammalian or insect host cell comprising a first nucleotide sequence encoding mammalian endopeptidase protein precursor processing enzyme, PACE, capable of cleaving precursor polypeptides at basic amino acid pairs, operably linked to a heterologous expression control sequence permitting expression of the nucleotide sequence and a second nucleotide sequence encoding the precursor of said selected biologically active protein, said protein requiring gamma-carboxylation for biological activity, operably linked to a heterologous expression control sequence permitting expression of the second nucleotide sequence, wherein the action of said PACE on the expression product of the second nucleotide sequence permits the production of said biologically active protein.

37. The method according to claim 36 wherein the encoded PACE retains PACE biological activity and is selected from the group consisting of (a) SEQ ID NO: 2, (b) a soluble analog of SEQ ID NO: 2; and (c) an analog of SEQ ID NO: 2 encoded by a modified SEQ ID NO: 1 or SEQ ID NO: 3, which modification consists of 1 to 4 codon changes in a region of said encoding sequence not encompassing the active site of said PACE.

38. The method according to claim 36 wherein the first nucleotide sequence and the second nucleotide sequence are present on a single vector.

39. The method according to claim 36 wherein the first nucleotide sequence is present on a first vector and the second nucleotide sequence is present on a second vector.

40. The method according to claim 36 wherein said host cell is a mammalian cell.

41. The method according to claim 40 wherein said host cell is a Chinese Hamster Ovary cell.

42. A method of increasing the yield of a selected biologically active protein having a precursor which is a substrate for PACE comprising culturing a transformed mammalian or insect host cell comprising a first nucleotide sequence encoding mammalian endopeptidase protein precursor processing enzyme, PACE, capable of cleaving precursor polypeptides at basic amino acid pairs, operably linked to a heterologous expression control sequence permitting expression of the nucleotide sequence and a second nucleotide sequence encoding the precursor of said selected biologically active protein, operably linked to a heterologous expression control sequence permitting expression of the second nucleotide sequence, wherein the action of said PACE on the expression product of the second nucleotide sequence permits the production of said biologically active protein, wherein the biologically active protein is a blood coagulation protein selected from the group consisting of Factor IX, Protein C, Protein S, Prothrombin Factor X, and Factor VII.

43. The method according to claim 42 wherein the first nucleotide sequence is present on a first vector and the second nucleotide sequence is present on a second vector.

44. The method according to claim 42 wherein the first nucleotide sequence and the second nucleotide sequence are present on a single vector.

45. The method according to claim 42 wherein the biologically active protein is Factor IX.

46. The method according to claim 42 wherein said host cell is a mammalian cell.

47. The method according to claim 46 wherein said host cell is a Chinese Hamster Ovary cell.

48. The method according to claim 42 wherein said PACE retains PACE biological activity and is selected from the group consisting of (a) SEQ ID NO: 2, (b) a soluble analog of SEQ ID NO: 2, and (c) an analog of SEQ ID NO: 2 encoded by a modified SEQ ID NO: 1 or SEQ ID NO: 3, which modification consists of 1 to 4 codon changes in a region of said encoding sequence not encompassing the active site of said PACE.

49. A method of increasing the yield of a biologically active protein having a precursor which is a substrate for PACE comprising culturing a transformed mammalian or insect host cell comprising a first nucleotide sequence encoding mammalian endopeptidase protein precursor processing enzyme, PACE, capable of cleaving precursor polypeptides at basic amino acid pairs, operably linked to a heterologous expression control sequence permitting expression of the nucleotide sequence, and a second nucleotide sequence encoding the precursor of von Willebrand factor, operably linked to a heterologous expression control sequence permitting expression of the second nucleotide sequence, wherein the action of said PACE on the expression product of the second nucleotide sequence permits the production of biologically active von Willebrand Factor.

50. The method according to claim 49 wherein said the first nucleotide sequence is present on a first vector and the second nucleotide sequence is present on a second vector.

51. The method according to claim 49 wherein the first nucleotide sequence and the second nucleotide sequence are present on a single vector.

52. The method according to claim 49 wherein said PACE retains PACE biological activity and is selected from the group consisting of (a) SEQ ID NO: 2, (b) a soluble analog of SEQ ID NO: 2, and (c) an analog of SEQ ID NO: 2 encoded by a modified SEQ ID NO: 1 or SEQ ID NO: 3, which modification consists of 1 to 4 codon changes in a region of said encoding sequence not encompassing the active site of said PACE.

53. The method according to claim 49 wherein said host cell is a mammalian cell.

54. The method according to claim 53 wherein said host cell is a Chinese Hamster Ovary cell.

55. A method of increasing the yield of a biologically active protein having a precursor which is a substrate for PACE comprising culturing a transformed mammalian or insect host cell comprising a first nucleotide sequence encoding mammalian endopeptidase protein precursor processing enzyme, PACE, capable of cleaving precursor polypeptides at basic amino acid pairs, operably linked to a heterologous expression control sequence permitting expression of the nucleotide sequence and a second nucleotide sequence encoding the precursor of bone-gamma carboxyglutamate protein, operably linked to a heterologous expression control sequence permitting expression of the second nucleotide sequence, wherein the action of said PACE on the expression product of the second nucleotide sequence permits the production of biologically active bone-gamma carboxyglutamate protein.

56. The method according to claim 55 wherein said the first nucleotide sequence is present on a first vector and the second nucleotide sequence is present on a second vector.

57. The method according to claim 55 wherein the first nucleotide sequence and the second nucleotide sequence are present on a single vector.

58. The method according to claim 55 wherein said PACE retains PACE biological activity and is selected from the group consisting of (a) SEQ ID NO: 2, (b) a soluble analog of SEQ ID NO: 2, and (c) an analog of SEQ ID NO: 2 encoded by a modified SEQ ID NO: 1 or SEQ ID NO: 3, which modification consists of 1 to 4 codon changes in a region of said encoding sequence not encompassing the active site of said PACE.

59. The method according to claim 55 wherein said host cell is a mammalian cell.

60. The method according to claim 59 wherein said host cell is a Chinese Hamster Ovary cell.

* * * * *

UNITED STATES PATENT AND TRADEMARK OFFICE
CERTIFICATE OF CORRECTION

PATENT NO. : 5,460,950
DATED : October 24, 1995
INVENTOR(S) : Philip J. Barr, Anthony J. Brake, Randal J. Kaufman, Louise Wasley, Patricia Tekamp-Olson, and Polly A. Wong It is certified that error appears in the above-indentified patent and that said Letters Patent is hereby corrected as shown below:

Col. 17, line 4, delete "600573" and insert thereof -- 60057 --.

Col. 58, line 2, delete "yon" and insert thereof -- von --.

Col. 59, line 2, delete "liked" and insert thereof -- linked --.

Signed and Sealed this

Ninth Day of April, 1996

Attest:

BRUCE LEHMAN

Attesting Officer    Commissioner of Patents and Trademarks

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
  ( A ) LENGTH: 2385 base pairs
  ( B ) TYPE: nucleic acid
  ( C ) STRANDEDNESS: double
  ( D ) TOPOLOGY: unknown ( i i ) MOLECULE TYPE: DNA (genomic)

( i x ) FEATURE:

-continued (A) NAME/KEY: CDS
(B) LOCATION: 1..2382

(x) PUBLICATION INFORMATION:
(A) AUTHORS: van den Ouweland W., A. M.
(C) JOURNAL: Nucleic Acids Res.
(D) VOLUME: 18
(F) PAGES: 664-
(G) DATE: 1990

(xi) SEQUENCE DESCRIPTION: SEQ ID NO:1:

```
ATG GAG CTG AGG CCC TGG TTG CTA TGG GTG GTA GCA GCA ACA GGA ACC      48
Met Glu Leu Arg Pro Trp Leu Leu Trp Val Val Ala Ala Thr Gly Thr
 1               5                  10                  15

TTG GTC CTG CTA GCA GCT GAT GCT CAG GGC CAG AAG GTC TTC ACC AAC      96
Leu Val Leu Leu Ala Ala Asp Ala Gln Gly Gln Lys Val Phe Thr Asn
             20                  25                  30

ACG TGG GCT GTG CGC ATC CCT GGA GGC CCA GCG GTG GCC AAC AGT GTG     144
Thr Trp Ala Val Arg Ile Pro Gly Gly Pro Ala Val Ala Asn Ser Val
         35                  40                  45

GCA CGG AAG CAT GGG TTC CTC AAC CTG GGC CAG ATC TTC GGG GAC TAT     192
Ala Arg Lys His Gly Phe Leu Asn Leu Gly Gln Ile Phe Gly Asp Tyr
     50                  55                  60

TAC CAC TTC TGG CAT CGA GGA GTG ACG AAG CGG TCC CTG TCG CCT CAC     240
Tyr His Phe Trp His Arg Gly Val Thr Lys Arg Ser Leu Ser Pro His
 65                  70                  75                  80

CGC CCG CGG CAC AGC CGG CTG CAG AGG GAG CCT CAA GTA CAG TGG CTG     288
Arg Pro Arg His Ser Arg Leu Gln Arg Glu Pro Gln Val Gln Trp Leu
                 85                  90                  95

GAA CAG CAG GTG GCA AAG CGA CGG ACT AAA CGG GAC GTG TAC CAG GAG     336
Glu Gln Gln Val Ala Lys Arg Arg Thr Lys Arg Asp Val Tyr Gln Glu
                100                 105                 110

CCC ACA GAC CCC AAG TTT CCT CAG CAG TGG TAC CTG TCT GGT GTC ACT     384
Pro Thr Asp Pro Lys Phe Pro Gln Gln Trp Tyr Leu Ser Gly Val Thr
            115                 120                 125

CAG CGG GAC CTG AAT GTG AAG GCG GCC TGG GCG CAG GGC TAC ACA GGG     432
Gln Arg Asp Leu Asn Val Lys Ala Ala Trp Ala Gln Gly Tyr Thr Gly
        130                 135                 140

CAC GGC ATT GTG GTC TCC ATT CTG GAC GAT GGC ATC GAG AAG AAC CAC     480
His Gly Ile Val Val Ser Ile Leu Asp Asp Gly Ile Glu Lys Asn His
145                 150                 155                 160

CCG GAC TTG GCA GGC AAT TAT GAT CCT GGG GCC AGT TTT GAT GTC AAT     528
Pro Asp Leu Ala Gly Asn Tyr Asp Pro Gly Ala Ser Phe Asp Val Asn
                165                 170                 175

GAC CAG GAC CCT GAC CCC CAG CCT CGG TAC ACA CAG ATG AAT GAC AAC     576
Asp Gln Asp Pro Asp Pro Gln Pro Arg Tyr Thr Gln Met Asn Asp Asn
            180                 185                 190

AGG CAC GGC ACA CGG TGT GCG GGG GAA GTG GCT GCG GTG GCC AAC AAC     624
Arg His Gly Thr Arg Cys Ala Gly Glu Val Ala Ala Val Ala Asn Asn
        195                 200                 205

GGT GTC TGT GGT GTA GGT GTG GCC TAC AAC GCC CGC ATT GGA GGG GTG     672
Gly Val Cys Gly Val Gly Val Ala Tyr Asn Ala Arg Ile Gly Gly Val
210                 215                 220

CGC ATG CTG GAT GGC GAG GTG ACA GAT GCA GTG GAG GCA CGC TCG CTG     720
Arg Met Leu Asp Gly Glu Val Thr Asp Ala Val Glu Ala Arg Ser Leu
225                 230                 235                 240

GGC CTG AAC CCC AAC CAC ATC CAC ATC TAC AGT GCC AGC TGG GGC CCC     768
Gly Leu Asn Pro Asn His Ile His Ile Tyr Ser Ala Ser Trp Gly Pro
                245                 250                 255

GAG GAT GAC GGC AAG ACA GTG GAT GGG CCA GCC CGC CTC GCC GAG GAG     816
Glu Asp Asp Gly Lys Thr Val Asp Gly Pro Ala Arg Leu Ala Glu Glu
            260                 265                 270
```

```
GCC TTC TTC CGT GGG GTT AGC CAG GGC CGA GGG GGG CTG GGC TCC ATC        864
Ala Phe Phe Arg Gly Val Ser Gln Gly Arg Gly Gly Leu Gly Ser Ile
        275                     280                     285

TTT GTC TGG GCC TCG GGG AAC GGG GGC CGG GAA CAT GAC AGC TGC AAC        912
Phe Val Trp Ala Ser Gly Asn Gly Gly Arg Glu His Asp Ser Cys Asn
        290                     295                     300

TGC GAC GGC TAC ACC AAC AGT ATC TAC ACG CTG TCC ATC AGC AGC GCC        960
Cys Asp Gly Tyr Thr Asn Ser Ile Tyr Thr Leu Ser Ile Ser Ser Ala
305                     310                     315                     320

ACG CAG TTT GGC AAC GTG CCG TGG TAC AGC GAG GCC TGC TCG TCC ACA       1008
Thr Gln Phe Gly Asn Val Pro Trp Tyr Ser Glu Ala Cys Ser Ser Thr
                        325                     330                     335

CTG GCC ACG ACC TAC AGC AGT GGC AAC CAG AAT GAG AAG CAG ATC GTG       1056
Leu Ala Thr Thr Tyr Ser Ser Gly Asn Gln Asn Glu Lys Gln Ile Val
                340                     345                     350

ACG ACT GAC TTG CGG CAG AAG TGC ACG GAG TCT CAC ACG GGC ACC TCA       1104
Thr Thr Asp Leu Arg Gln Lys Cys Thr Glu Ser His Thr Gly Thr Ser
                355                     360                     365

GCC TCT GCC CCC TTA GCA GCC GGC ATC ATT GCT CTC ACC CTG GAG GCC       1152
Ala Ser Ala Pro Leu Ala Ala Gly Ile Ile Ala Leu Thr Leu Glu Ala
        370                     375                     380

AAT AAG AAC CTC ACA TGG CGG GAC ATG CAA CAC CTG GTG GTA CAG ACC       1200
Asn Lys Asn Leu Thr Trp Arg Asp Met Gln His Leu Val Val Gln Thr
385                     390                     395                     400

TCG AAG CCA GCC CAC CTC AAT GCC AAC GAC TGG GCC ACC AAT GGT GTG       1248
Ser Lys Pro Ala His Leu Asn Ala Asn Asp Trp Ala Thr Asn Gly Val
                        405                     410                     415

GGG CGG AAA GTG AGC CAC TCA TAT GGC TAC GGG CTT TTG GAC GCA GGC       1296
Gly Arg Lys Val Ser His Ser Tyr Gly Tyr Gly Leu Leu Asp Ala Gly
                420                     425                     430

GCC ATG GTG GCC CTG GCC CAG AAT TGG ACC ACA GTG GCC CCC CAG CGG       1344
Ala Met Val Ala Leu Ala Gln Asn Trp Thr Thr Val Ala Pro Gln Arg
                435                     440                     445

AAG TGC ATC ATC GAC ATC CTC ACC GAG CCC AAA GAC ATC GGG AAA CGG       1392
Lys Cys Ile Ile Asp Ile Leu Thr Glu Pro Lys Asp Ile Gly Lys Arg
        450                     455                     460

CTC GAG GTG CGG AAG ACC GTG ACC GCG TGC CTG GGC GAG CCC AAC CAC       1440
Leu Glu Val Arg Lys Thr Val Thr Ala Cys Leu Gly Glu Pro Asn His
465                     470                     475                     480

ATC ACT CGG CTG GAG CAC GCT CAG GCG CGG CTC ACC CTG TCC TAT AAT       1488
Ile Thr Arg Leu Glu His Ala Gln Ala Arg Leu Thr Leu Ser Tyr Asn
                        485                     490                     495

CGC CGT GGC GAC CTG GCC ATC CAC CTG GTC AGC CCC ATG GGC ACC CGC       1536
Arg Arg Gly Asp Leu Ala Ile His Leu Val Ser Pro Met Gly Thr Arg
                500                     505                     510

TCC ACC CTG CTG GCA GCC AGG CCA CAT GAC TAC TCC GCA GAT GGG TTT       1584
Ser Thr Leu Leu Ala Ala Arg Pro His Asp Tyr Ser Ala Asp Gly Phe
                515                     520                     525

AAT GAC TGG GCC TTC ATG ACA ACT CAT TCC TGG GAT GAG GAT CCC TCT       1632
Asn Asp Trp Ala Phe Met Thr Thr His Ser Trp Asp Glu Asp Pro Ser
        530                     535                     540

GGC GAG TGG GTC CTA GAG ATT GAA AAC ACC AGC GAA GCC AAC AAC TAT       1680
Gly Glu Trp Val Leu Glu Ile Glu Asn Thr Ser Glu Ala Asn Asn Tyr
545                     550                     555                     560

GGG ACG CTG ACC AAG TTC ACC CTC GTA CTC TAT GGC ACC GCC CCT GAG       1728
Gly Thr Leu Thr Lys Phe Thr Leu Val Leu Tyr Gly Thr Ala Pro Glu
                        565                     570                     575

GGG CTG CCC GTA CCT CCA GAA AGC AGT GGC TGC AAG ACC CTC ACG TCC       1776
Gly Leu Pro Val Pro Pro Glu Ser Ser Gly Cys Lys Thr Leu Thr Ser
```

|  |  |  |  |  |  |  |  |  |  |  |  |  |  |  |  |
|---|---|---|---|---|---|---|---|---|---|---|---|---|---|---|---|
|  |  |  | 580 |  |  |  |  | 585 |  |  |  |  | 590 |  |  |
| AGT | CAG | GCC | TGT | GTG | GTG | TGC | GAG | GAA | GGC | TTC | TCC | CTG | CAC | CAG | AAG | 1824 |
| Ser | Gln | Ala | Cys | Val | Val | Cys | Glu | Glu | Gly | Phe | Ser | Leu | His | Gln | Lys |  |
|  |  | 595 |  |  |  |  | 600 |  |  |  |  | 605 |  |  |  |  |
| AGC | TGT | GTC | CAG | CAC | TGC | CCT | CCA | GGC | TTC | GCC | CCC | CAA | GTC | CTC | GAT | 1872 |
| Ser | Cys | Val | Gln | His | Cys | Pro | Pro | Gly | Phe | Ala | Pro | Gln | Val | Leu | Asp |  |
|  | 610 |  |  |  |  | 615 |  |  |  |  | 620 |  |  |  |  |  |
| ACG | CAC | TAT | AGC | ACC | GAG | AAT | GAC | GTG | GAG | ACC | ATC | CGG | GCC | AGC | GTC | 1920 |
| Thr | His | Tyr | Ser | Thr | Glu | Asn | Asp | Val | Glu | Thr | Ile | Arg | Ala | Ser | Val |  |
| 625 |  |  |  |  | 630 |  |  |  |  | 635 |  |  |  |  | 640 |  |
| TGC | GCC | CCC | TGC | CAC | GCC | TCA | TGT | GCC | ACA | TGC | CAG | GGG | CCG | GCC | CTG | 1968 |
| Cys | Ala | Pro | Cys | His | Ala | Ser | Cys | Ala | Thr | Cys | Gln | Gly | Pro | Ala | Leu |  |
|  |  |  |  | 645 |  |  |  |  | 650 |  |  |  |  | 655 |  |  |
| ACA | GAC | TGC | CTC | AGC | TGC | CCC | AGC | CAC | GCC | TCC | TTG | GAC | CCT | GTG | GAG | 2016 |
| Thr | Asp | Cys | Leu | Ser | Cys | Pro | Ser | His | Ala | Ser | Leu | Asp | Pro | Val | Glu |  |
|  |  |  | 660 |  |  |  |  | 665 |  |  |  |  | 670 |  |  |  |
| CAG | ACT | TGC | TCC | CGG | CAA | AGC | CAG | AGC | AGC | CGA | GAG | TCC | CCG | CCA | CAG | 2064 |
| Gln | Thr | Cys | Ser | Arg | Gln | Ser | Gln | Ser | Ser | Arg | Glu | Ser | Pro | Pro | Gln |  |
|  |  | 675 |  |  |  |  | 680 |  |  |  |  | 685 |  |  |  |  |
| CAG | CAG | CCA | CCT | CGG | CTG | CCC | CCG | GAG | GTG | GAG | GCG | GGG | CAA | CGG | CTG | 2112 |
| Gln | Gln | Pro | Pro | Arg | Leu | Pro | Pro | Glu | Val | Glu | Ala | Gly | Gln | Arg | Leu |  |
|  | 690 |  |  |  |  | 695 |  |  |  |  | 700 |  |  |  |  |  |
| CGG | GCA | GGG | CTG | CTG | CCC | TCA | CAC | CTG | CCT | GAG | GTG | GTG | GCC | GGC | CTC | 2160 |
| Arg | Ala | Gly | Leu | Leu | Pro | Ser | His | Leu | Pro | Glu | Val | Val | Ala | Gly | Leu |  |
| 705 |  |  |  |  | 710 |  |  |  |  | 715 |  |  |  |  | 720 |  |
| AGC | TGC | GCC | TTC | ATC | GTG | CTG | GTC | TTC | GTC | ACT | GTC | TTC | CTG | GTC | CTG | 2208 |
| Ser | Cys | Ala | Phe | Ile | Val | Leu | Val | Phe | Val | Thr | Val | Phe | Leu | Val | Leu |  |
|  |  |  |  | 725 |  |  |  |  | 730 |  |  |  |  | 735 |  |  |
| CAG | CTG | CGC | TCT | GGC | TTT | AGT | TTT | CGG | GGG | GTG | AAG | GTG | TAC | ACC | ATG | 2256 |
| Gln | Leu | Arg | Ser | Gly | Phe | Ser | Phe | Arg | Gly | Val | Lys | Val | Tyr | Thr | Met |  |
|  |  |  | 740 |  |  |  |  | 745 |  |  |  |  | 750 |  |  |  |
| GAC | CGT | GGC | CTC | ATC | TCC | TAC | AAG | GGG | CTG | CCC | CCT | GAA | GCC | TGG | CAG | 2304 |
| Asp | Arg | Gly | Leu | Ile | Ser | Tyr | Lys | Gly | Leu | Pro | Pro | Glu | Ala | Trp | Gln |  |
|  | 755 |  |  |  |  | 760 |  |  |  |  |  |  | 765 |  |  |  |
| GAG | GAG | TGC | CCG | TCT | GAC | TCA | GAA | GAG | GAC | GAG | GGC | CGG | GGC | GAG | AGG | 2352 |
| Glu | Glu | Cys | Pro | Ser | Asp | Ser | Glu | Glu | Asp | Glu | Gly | Arg | Gly | Glu | Arg |  |
| 770 |  |  |  |  | 775 |  |  |  |  | 780 |  |  |  |  |  |  |
| ACC | GCC | TTT | ATC | AAA | GAC | CAG | AGC | GCC | CTC | TGA |  |  |  |  |  | 2385 |
| Thr | Ala | Phe | Ile | Lys | Asp | Gln | Ser | Ala | Leu |  |  |  |  |  |  |  |
| 785 |  |  |  | 790 |  |  |  |  |  |  |  |  |  |  |  |  |

(2) INFORMATION FOR SEQ ID NO:2:

(i) SEQUENCE CHARACTERISTICS:
        (A) LENGTH: 794 amino acids
        (B) TYPE: amino acid
        (D) TOPOLOGY: linear (ii) MOLECULE TYPE: protein (xi) SEQUENCE DESCRIPTION: SEQ ID NO:2:

|  |  |  |  |  |  |  |  |  |  |  |  |  |  |  |
|---|---|---|---|---|---|---|---|---|---|---|---|---|---|---|
| Met | Glu | Leu | Arg | Pro | Trp | Leu | Leu | Trp | Val | Val | Ala | Ala | Thr | Gly |
| 1 |  |  |  | 5 |  |  |  |  | 10 |  |  |  |  | 15 |
| Thr | Leu | Val | Leu | Leu | Ala | Ala | Asp | Ala | Gln | Gly | Gln | Lys | Val | Phe |
|  |  |  | 20 |  |  |  |  | 25 |  |  |  |  | 30 |  |
| Thr | Asn | Thr | Trp | Ala | Val | Arg | Ile | Pro | Gly | Gly | Pro | Ala | Val | Ala |
|  |  | 35 |  |  |  |  | 40 |  |  |  |  | 45 |  |  |
| Asn | Ser | Val | Ala | Arg | Lys | His | Gly | Phe | Leu | Asn | Leu | Gly | Gln | Ile |
|  |  |  | 50 |  |  |  |  | 55 |  |  |  |  | 60 |  |
| Phe | Gly | Asp | Tyr | Tyr | His | Phe | Trp | His | Arg | Gly | Val | Thr | Lys | Arg |
|  |  |  |  |  |  |  |  |  |  |  |  |  |  |  |
| Ser | Leu | Ser | Pro | His |  |  |  |  |  |  |  |  |  |  |

|   |   |   |   |   | 65 |   |   |   |   | 70 |   |   |   |   | 75 |   |   |   |   | 80 |
|---|---|---|---|---|---|---|---|---|---|---|---|---|---|---|---|---|---|---|---|---|
| Arg | Pro | Arg | His | Ser | Arg | Leu | Gln | Arg | Glu | Pro | Gln | Val | Gln | Trp | Leu |
|   |   |   |   | 85 |   |   |   |   | 90 |   |   |   |   | 95 |   |

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
        275                 280                 285

Phe Val Trp Ala Ser Gly Asn Gly Gly Arg Glu His Asp Ser Cys Asn
    290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
            340                 345                 350

Thr Thr Asp Leu Arg Gln Lys Cys Thr Glu Ser His Thr Gly Thr Ser
        355                 360                 365

Ala Ser Ala Pro Leu Ala Ala Gly Ile Ile Ala Leu Thr Leu Glu Ala
    370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415

Gly Arg Lys Val Ser His Ser Tyr Gly Tyr Gly Leu Leu Asp Ala Gly
            420                 425                 430

Ala Met Val Ala Leu Ala Gln Asn Trp Thr Thr Val Ala Pro Gln Arg
        435                 440                 445

Lys Cys Ile Ile Asp Ile Leu Thr Glu Pro Lys Asp Ile Gly Lys Arg
    450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
                485                 490                 495

| Arg | Arg | Gly | Asp 500 | Leu | Ala | Ile | His | Leu 505 | Val | Ser | Pro | Met | Gly 510 | Thr | Arg |
|---|---|---|---|---|---|---|---|---|---|---|---|---|---|---|---|
| Ser | Thr | Leu 515 | Leu | Ala | Ala | Arg | Pro 520 | His | Asp | Tyr | Ser | Ala 525 | Asp | Gly | Phe |
| Asn | Asp 530 | Trp | Ala | Phe | Met | Thr 535 | Thr | His | Ser | Trp | Asp 540 | Glu | Asp | Pro | Ser |
| Gly 545 | Glu | Trp | Val | Leu | Glu 550 | Ile | Glu | Asn | Thr | Ser 555 | Glu | Ala | Asn | Asn | Tyr 560 |
| Gly | Thr | Leu | Thr | Lys 565 | Phe | Thr | Leu | Val | Leu 570 | Tyr | Gly | Thr | Ala | Pro 575 | Glu |
| Gly | Leu | Pro | Val 580 | Pro | Pro | Glu | Ser | Ser 585 | Gly | Cys | Lys | Thr | Leu 590 | Thr | Ser |
| Ser | Gln | Ala 595 | Cys | Val | Val | Cys | Glu 600 | Glu | Gly | Phe | Ser | Leu 605 | His | Gln | Lys |
| Ser | Cys 610 | Val | Gln | His | Cys | Pro 615 | Pro | Gly | Phe | Ala | Pro 620 | Gln | Val | Leu | Asp |
| Thr 625 | His | Tyr | Ser | Thr | Glu 630 | Asn | Asp | Val | Glu | Thr 635 | Ile | Arg | Ala | Ser | Val 640 |
| Cys | Ala | Pro | Cys | His 645 | Ala | Ser | Cys | Ala | Thr 650 | Cys | Gln | Gly | Pro | Ala 655 | Leu |
| Thr | Asp | Cys | Leu 660 | Ser | Cys | Pro | Ser | His 665 | Ala | Ser | Leu | Asp | Pro 670 | Val | Glu |
| Gln | Thr | Cys 675 | Ser | Arg | Gln | Ser | Gln 680 | Ser | Ser | Arg | Glu | Ser 685 | Pro | Pro | Gln |
| Gln 690 | Gln | Pro | Pro | Arg | Leu 695 | Pro | Pro | Glu | Val | Glu 700 | Ala | Gly | Gln | Arg | Leu |
| Arg 705 | Ala | Gly | Leu | Leu | Pro 710 | Ser | His | Leu | Pro | Glu 715 | Val | Val | Ala | Gly | Leu 720 |
| Ser | Cys | Ala | Phe | Ile 725 | Val | Leu | Val | Phe | Val 730 | Thr | Val | Phe | Leu | Val 735 | Leu |
| Gln | Leu | Arg | Ser 740 | Gly | Phe | Ser | Phe | Arg 745 | Gly | Val | Lys | Val | Tyr 750 | Thr | Met |
| Asp | Arg | Gly 755 | Leu | Ile | Ser | Tyr | Lys 760 | Gly | Leu | Pro | Pro | Glu 765 | Ala | Trp | Gln |
| Glu | Glu 770 | Cys | Pro | Ser | Asp | Ser 775 | Glu | Glu | Asp | Glu | Gly 780 | Arg | Gly | Glu | Arg |
| Thr 785 | Ala | Phe | Ile | Lys | Asp 790 | Gln | Ser | Ala | Leu |  |  |  |  |  |  |

( 2 ) INFORMATION FOR SEQ ID NO:3:

( i ) SEQUENCE CHARACTERISTICS:
        ( A ) LENGTH: 4405 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 408..2789

( x i ) SEQUENCE DESCRIPTION: SEQ ID NO:3:

| GAATTCGGAG | ATCTACAGGG | CTGCCCCCGC | CCGCGCCGGA | GCTGGAGCCC | AGGCCGAGCC | 60 |
|---|---|---|---|---|---|---|
| CTGCCCTGGT | CGCCGGCCGG | GCCGAGGCCG | CGCCGCCGCG | CCTCCCCGCC | TCCGCGCCGT | 120 |

-continued

```
GACGCTGCCG CCGGGCGCGG GGACCGCGCC GAGCCCAGGC CCCCGCCGCC GGGCTCTCCG          180

CTCGGCCGAG GGGCGCCCGA GCCGCCGCGG CGGTCGCCTG GAAAAGTTTC CCCGCCAGGG          240

CTCCCCAGGG GTCGGCACTC TTCACCCTCC CGAGCCCTGC CCGTCTCGGC CCCATGCCCC          300

CACCAGTCAG CCCCGGGCCA CAGGCAGTGA GCAGGCACCT GGGAGCCGAG GCCTGTGACC          360

AGGCCAAGGA GACGGGCGCT CCAGGGTCCC AGCCACCTGT CCCCCCC ATG GAG CTG           416
                                                    Met Glu Leu
                                                     1
```

|     |     |     |     |     |     |     |     |     |     |     |     |     |     |     |     |
|-----|-----|-----|-----|-----|-----|-----|-----|-----|-----|-----|-----|-----|-----|-----|-----|
| AGG | CCC | TGG | TTG | CTA | TGG | GTG | GTA | GCA | GCA | ACA | GGA | ACC | TTG | GTC | CTG |   464
| Arg | Pro | Trp | Leu | Leu | Trp | Val | Val | Ala | Ala | Thr | Gly | Thr | Leu | Val | Leu |
|     | 5   |     |     |     | 10  |     |     |     |     | 15  |     |     |     |     |     |
| CTA | GCA | GCT | GAT | GCT | CAG | GGC | CAG | AAG | GTC | TTC | ACC | AAC | ACG | TGG | GCT |   512
| Leu | Ala | Ala | Asp | Ala | Gln | Gly | Gln | Lys | Val | Phe | Thr | Asn | Thr | Trp | Ala |
| 20  |     |     |     |     | 25  |     |     |     |     | 30  |     |     |     |     | 35  |
| GTG | CGC | ATC | CCT | GGA | GGC | CCA | GCG | GTG | GCC | AAC | AGT | GTG | GCA | CGG | AAG |   560
| Val | Arg | Ile | Pro | Gly | Gly | Pro | Ala | Val | Ala | Asn | Ser | Val | Ala | Arg | Lys |
|     |     |     |     | 40  |     |     |     |     | 45  |     |     |     |     | 50  |     |
| CAT | GGG | TTC | CTC | AAC | CTG | GGC | CAG | ATC | TTC | GGG | GAC | TAT | TAC | CAC | TTC |   608
| His | Gly | Phe | Leu | Asn | Leu | Gly | Gln | Ile | Phe | Gly | Asp | Tyr | Tyr | His | Phe |
|     |     |     | 55  |     |     |     | 60  |     |     |     |     |     | 65  |     |     |
| TGG | CAT | CGA | GGA | GTG | ACG | AAG | CGG | TCC | CTG | TCG | CCT | CAC | CGC | CCG | CGG |   656
| Trp | His | Arg | Gly | Val | Thr | Lys | Arg | Ser | Leu | Ser | Pro | His | Arg | Pro | Arg |
|     |     | 70  |     |     |     | 75  |     |     |     |     | 80  |     |     |     |     |
| CAC | AGC | CGG | CTG | CAG | AGG | GAG | CCT | CAA | GTA | CAG | TGG | CTG | GAA | CAG | CAG |   704
| His | Ser | Arg | Leu | Gln | Arg | Glu | Pro | Gln | Val | Gln | Trp | Leu | Glu | Gln | Gln |
|     | 85  |     |     |     | 90  |     |     |     |     | 95  |     |     |     |     |     |
| GTG | GCA | AAG | CGA | CGG | ACT | AAA | CGG | GAC | GTG | TAC | CAG | GAG | CCC | ACA | GAC |   752
| Val | Ala | Lys | Arg | Arg | Thr | Lys | Arg | Asp | Val | Tyr | Gln | Glu | Pro | Thr | Asp |
| 100 |     |     |     |     | 105 |     |     |     |     | 110 |     |     |     |     | 115 |
| CCC | AAG | TTT | CCT | CAG | CAG | TGG | TAC | CTG | TCT | GGT | GTC | ACT | CAG | CGG | GAC |   800
| Pro | Lys | Phe | Pro | Gln | Gln | Trp | Tyr | Leu | Ser | Gly | Val | Thr | Gln | Arg | Asp |
|     |     |     |     | 120 |     |     |     |     | 125 |     |     |     |     | 130 |     |
| CTG | AAT | GTG | AAG | GCG | GCC | TGG | GCG | CAG | GGC | TAC | ACA | GGG | CAC | GGC | ATT |   848
| Leu | Asn | Val | Lys | Ala | Ala | Trp | Ala | Gln | Gly | Tyr | Thr | Gly | His | Gly | Ile |
|     |     |     | 135 |     |     |     | 140 |     |     |     |     |     | 145 |     |     |
| GTG | GTC | TCC | ATT | CTG | GAC | GAT | GGC | ATC | GAG | AAG | AAC | CAC | CCG | GAC | TTG |   896
| Val | Val | Ser | Ile | Leu | Asp | Asp | Gly | Ile | Glu | Lys | Asn | His | Pro | Asp | Leu |
|     |     | 150 |     |     |     | 155 |     |     |     |     | 160 |     |     |     |     |
| GCA | GGC | AAT | TAT | GAT | CCT | GGG | GCC | AGT | TTT | GAT | GTC | AAT | GAC | CAG | GAC |   944
| Ala | Gly | Asn | Tyr | Asp | Pro | Gly | Ala | Ser | Phe | Asp | Val | Asn | Asp | Gln | Asp |
|     | 165 |     |     |     | 170 |     |     |     |     | 175 |     |     |     |     |     |
| CCT | GAC | CCC | CAG | CCT | CGG | TAC | ACA | CAG | ATG | AAT | GAC | AAC | AGG | CAC | GGC |   992
| Pro | Asp | Pro | Gln | Pro | Arg | Tyr | Thr | Gln | Met | Asn | Asp | Asn | Arg | His | Gly |
| 180 |     |     |     |     | 185 |     |     |     | 190 |     |     |     |     | 195 |     |
| ACA | CGG | TGT | GCG | GGG | GAA | GTG | GCT | GCG | GTG | GCC | AAC | AAC | GGT | GTC | TGT |  1040
| Thr | Arg | Cys | Ala | Gly | Glu | Val | Ala | Ala | Val | Ala | Asn | Asn | Gly | Val | Cys |
|     |     |     |     | 200 |     |     |     |     | 205 |     |     |     |     | 210 |     |
| GGT | GTA | GGT | GTG | GCC | TAC | AAC | GCC | CGC | ATT | GGA | GGG | GTG | CGC | ATG | CTG |  1088
| Gly | Val | Gly | Val | Ala | Tyr | Asn | Ala | Arg | Ile | Gly | Gly | Val | Arg | Met | Leu |
|     |     |     | 215 |     |     |     | 220 |     |     |     |     |     | 225 |     |     |
| GAT | GGC | GAG | GTG | ACA | GAT | GCA | GTG | GAG | GCA | CGC | TCG | CTG | GGC | CTG | AAC |  1136
| Asp | Gly | Glu | Val | Thr | Asp | Ala | Val | Glu | Ala | Arg | Ser | Leu | Gly | Leu | Asn |
|     |     | 230 |     |     |     | 235 |     |     |     |     | 240 |     |     |     |     |
| CCC | AAC | CAC | ATC | CAC | ATC | TAC | AGT | GCC | AGC | TGG | GGC | CCC | GAG | GAT | GAC |  1184
| Pro | Asn | His | Ile | His | Ile | Tyr | Ser | Ala | Ser | Trp | Gly | Pro | Glu | Asp | Asp |
|     | 245 |     |     |     | 250 |     |     |     |     | 255 |     |     |     |     |     |
| GGC | AAG | ACA | GTG | GAT | GGG | CCA | GCC | CGC | CTC | GCC | GAG | GAG | GCC | TTC | TTC |  1232
| Gly | Lys | Thr | Val | Asp | Gly | Pro | Ala | Arg | Leu | Ala | Glu | Glu | Ala | Phe | Phe |
| 260 |     |     |     |     | 265 |     |     |     |     | 270 |     |     |     |     | 275 |

```
CGT GGG GTT AGC CAG GGC CGA GGG GGG CTG GGC TCC ATC TTT GTC TGG                1280
Arg Gly Val Ser Gln Gly Arg Gly Gly Leu Gly Ser Ile Phe Val Trp
            280                 285                 290

GCC TCG GGG AAC GGG GGC CGG GAA CAT GAC AGC TGC AAC TGC GAC GGC                1328
Ala Ser Gly Asn Gly Gly Arg Glu His Asp Ser Cys Asn Cys Asp Gly
                295                 300                 305

TAC ACC AAC AGT ATC TAC ACG CTG TCC ATC AGC AGC GCC ACG CAG TTT                1376
Tyr Thr Asn Ser Ile Tyr Thr Leu Ser Ile Ser Ser Ala Thr Gln Phe
        310                 315                 320

GGC AAC GTG CCG TGG TAC AGC GAG GCC TGC TCG TCC ACA CTG GCC ACG                1424
Gly Asn Val Pro Trp Tyr Ser Glu Ala Cys Ser Ser Thr Leu Ala Thr
    325                 330                 335

ACC TAC AGC AGT GGC AAC CAG AAT GAG AAG CAG ATC GTG ACG ACT GAC                1472
Thr Tyr Ser Ser Gly Asn Gln Asn Glu Lys Gln Ile Val Thr Thr Asp
340                 345                 350                 355

TTG CGG CAG AAG TGC ACG GAG TCT CAC ACG GGC ACC TCA GCC TCT GCC                1520
Leu Arg Gln Lys Cys Thr Glu Ser His Thr Gly Thr Ser Ala Ser Ala
                360                 365                 370

CCC TTA GCA GCC GGC ATC ATT GCT CTC ACC CTG GAG GCC AAT AAG AAC                1568
Pro Leu Ala Ala Gly Ile Ile Ala Leu Thr Leu Glu Ala Asn Lys Asn
            375                 380                 385

CTC ACA TGG CGG GAC ATG CAA CAC CTG GTG GTA CAG ACC TCG AAG CCA                1616
Leu Thr Trp Arg Asp Met Gln His Leu Val Val Gln Thr Ser Lys Pro
        390                 395                 400

GCC CAC CTC AAT GCC AAC GAC TGG GCC ACC AAT GGT GTG GGC CGG AAA                1664
Ala His Leu Asn Ala Asn Asp Trp Ala Thr Asn Gly Val Gly Arg Lys
    405                 410                 415

GTG AGC CAC TCA TAT GGC TAC GGG CTT TTG GAC GCA GGC GCC ATG GTG                1712
Val Ser His Ser Tyr Gly Tyr Gly Leu Leu Asp Ala Gly Ala Met Val
420                 425                 430                 435

GCC CTG GCC CAG AAT TGG ACC ACA GTG GCC CCC CAG CGG AAG TGC ATC                1760
Ala Leu Ala Gln Asn Trp Thr Thr Val Ala Pro Gln Arg Lys Cys Ile
                440                 445                 450

ATC GAC ATC CTC ACC GAG CCC AAA GAC ATC GGG AAA CGG CTC GAG GTG                1808
Ile Asp Ile Leu Thr Glu Pro Lys Asp Ile Gly Lys Arg Leu Glu Val
            455                 460                 465

CGG AAG ACC GTG ACC GCG TGC CTG GGC GAG CCC AAC CAC ATC ACT CGG                1856
Arg Lys Thr Val Thr Ala Cys Leu Gly Glu Pro Asn His Ile Thr Arg
        470                 475                 480

CTG GAG CAC GCT CAG GCG CGG CTC ACC CTG TCC TAT AAT CGC CGT GGC                1904
Leu Glu His Ala Gln Ala Arg Leu Thr Leu Ser Tyr Asn Arg Arg Gly
    485                 490                 495

GAC CTG GCC ATC CAC CTG GTC AGC CCC ATG GGC ACC CGC TCC ACC CTG                1952
Asp Leu Ala Ile His Leu Val Ser Pro Met Gly Thr Arg Ser Thr Leu
500                 505                 510                 515

CTG GCA GCC AGG CCA CAT GAC TAC TCC GCA GAT GGG TTT AAT GAC TGG                2000
Leu Ala Ala Arg Pro His Asp Tyr Ser Ala Asp Gly Phe Asn Asp Trp
                520                 525                 530

GCC TTC ATG ACA ACT CAT TCC TGG GAT GAG GAT CCC TCT GGC GAG TGG                2048
Ala Phe Met Thr Thr His Ser Trp Asp Glu Asp Pro Ser Gly Glu Trp
            535                 540                 545

GTC CTA GAG ATT GAA AAC ACC AGC GAA GCC AAC AAC TAT GGG ACG CTG                2096
Val Leu Glu Ile Glu Asn Thr Ser Glu Ala Asn Asn Tyr Gly Thr Leu
        550                 555                 560

ACC AAG TTC ACC CTC GTA CTC TAT GGC ACC GCC CCT GAG GGG CTG CCC                2144
Thr Lys Phe Thr Leu Val Leu Tyr Gly Thr Ala Pro Glu Gly Leu Pro
    565                 570                 575

GTA CCT CCA GAA AGC AGT GGC TGC AAG ACC CTC ACG TCC AGT CAG GCC                2192
Val Pro Pro Glu Ser Ser Gly Cys Lys Thr Leu Thr Ser Ser Gln Ala
```

```
            580                          585                          590                          595
TGT  GTG  GTG  TGC  GAG  GAA  GGC  TTC  TCC  CTG  CAC  CAG  AAG  AGC  TGT  GTC          2240
Cys  Val  Val  Cys  Glu  Glu  Gly  Phe  Ser  Leu  His  Gln  Lys  Ser  Cys  Val
                    600                      605                      610

CAG  CAC  TGC  CCT  CCA  GGC  TTC  GCC  CCC  CAA  GTC  CTC  GAT  ACG  CAC  TAT          2288
Gln  His  Cys  Pro  Pro  Gly  Phe  Ala  Pro  Gln  Val  Leu  Asp  Thr  His  Tyr
               615                      620                      625

AGC  ACC  GAG  AAT  GAC  GTG  GAG  ACC  ATC  CGG  GCC  AGC  GTC  TGC  GCC  CCC          2336
Ser  Thr  Glu  Asn  Asp  Val  Glu  Thr  Ile  Arg  Ala  Ser  Val  Cys  Ala  Pro
          630                      635                      640

TGC  CAC  GCC  TCA  TGT  GCC  ACA  TGC  CAG  GGG  CCG  GCC  CTG  ACA  GAC  TGC          2384
Cys  His  Ala  Ser  Cys  Ala  Thr  Cys  Gln  Gly  Pro  Ala  Leu  Thr  Asp  Cys
     645                      650                      655

CTC  AGC  TGC  CCC  AGC  CAC  GCC  TCC  TTG  GAC  CCT  GTG  GAG  CAG  ACT  TGC          2432
Leu  Ser  Cys  Pro  Ser  His  Ala  Ser  Leu  Asp  Pro  Val  Glu  Gln  Thr  Cys
660                      665                      670                      675

TCC  CGG  CAA  AGC  CAG  AGC  AGC  CGA  GAG  TCC  CCG  CCA  CAG  CAG  CAG  CCA          2480
Ser  Arg  Gln  Ser  Gln  Ser  Ser  Arg  Glu  Ser  Pro  Pro  Gln  Gln  Gln  Pro
                    680                      685                      690

CCT  CGG  CTG  CCC  CCG  GAG  GTG  GAG  GCG  GGG  CAA  CGG  CTG  CGG  GCA  GGG          2528
Pro  Arg  Leu  Pro  Pro  Glu  Val  Glu  Ala  Gly  Gln  Arg  Leu  Arg  Ala  Gly
               695                      700                      705

CTG  CTG  CCC  TCA  CAC  CTG  CCT  GAG  GTG  GTG  GCC  GGC  CTC  AGC  TGC  GCC          2576
Leu  Leu  Pro  Ser  His  Leu  Pro  Glu  Val  Val  Ala  Gly  Leu  Ser  Cys  Ala
          710                      715                      720

TTC  ATC  GTG  CTG  GTC  TTC  GTC  ACT  GTC  TTC  CTG  GTC  CTG  CAG  CTG  CGC          2624
Phe  Ile  Val  Leu  Val  Phe  Val  Thr  Val  Phe  Leu  Val  Leu  Gln  Leu  Arg
     725                      730                      735

TCT  GGC  TTT  AGT  TTT  CGG  GGG  GTG  AAG  GTG  TAC  ACC  ATG  GAC  CGT  GGC          2672
Ser  Gly  Phe  Ser  Phe  Arg  Gly  Val  Lys  Val  Tyr  Thr  Met  Asp  Arg  Gly
740                      745                      750                      755

CTC  ATC  TCC  TAC  AAG  GGG  CTG  CCC  CCT  GAA  GCC  TGG  CAG  GAG  GAG  TGC          2720
Leu  Ile  Ser  Tyr  Lys  Gly  Leu  Pro  Pro  Glu  Ala  Trp  Gln  Glu  Glu  Cys
               760                      765                      770

CCG  TCT  GAC  TCA  GAA  GAG  GAC  GAG  GGC  CGG  GGC  GAG  AGG  ACC  GCC  TTT          2768
Pro  Ser  Asp  Ser  Glu  Glu  Asp  Glu  Gly  Arg  Gly  Glu  Arg  Thr  Ala  Phe
          775                      780                      785

ATC  AAA  GAC  CAG  AGC  GCC  CTC  TGATGAGCCC  ACTGCCCACC  CCCTCAAGCC                    2819
Ile  Lys  Asp  Gln  Ser  Ala  Leu
     790

AATCCCCTCC  TTGGGCACTT  TTTAATTCAC  CAAAGTATTT  TTTTATCTTG  GGACTGGGTT                    2879
TGGACCCCAG  CTGGGAGGCA  AGAGGGGTGG  AGACTGTTTC  CCATCCTACC  CTCGGGCCCA                    2939
CCTGGCCACC  TGAGGTGGGC  CCAGGACCAG  CTGGGGCGTG  GGGAGGGCCG  TACCCCACCC                    2999
TCAGCACCCC  TTCCATGTGG  AGAAAGGAGT  GAAACCTTTA  GGGCAGCTTG  CCCCGGCCCC                    3059
GGCCCCAGCC  AGAGTTCCTG  CGGAGTGAAG  AGGGGCAGCC  CTTGCTTGTT  GGGATTCCTG                    3119
ACCCAGGCCG  CAGCTCTTGC  CCTTCCCTGT  CCCTCTAAAG  CAATAATGGT  CCCATCCAGG                    3179
CAGTCGGGGG  CTGGCCTAGG  AGATATCTGA  GGGAGGAGGC  CACCTCTCCA  AGGGCTTCTG                    3239
CACCCTCCAC  CCTGTCCCCC  AGCTCTGGTG  AGTCTTGGCG  GCAGCAGCCA  TCATAGGAAG                    3299
GGACCAAGGC  AAGGCAGGTG  CCTCCAGGTG  TGCACGTGGC  ATGTGGCCTG  TGGCCTGTGT                    3359
CCCATGACCC  ACCCCTGTGC  TCCGTGCCTC  CACCACCACT  GGCCACCAGG  CTGGCGCAGC                    3419
CAAGGCCGAA  GCTCTGGCTG  AACCCTGTGC  TGGTGTCCTG  ACCACCCTCC  CCTCTCTTGC                    3479
ACCCGCCTCT  CCCGTCAGGG  CCCAAGTCCC  TGTTTTCTGA  GCCCGGGCTG  CCTGGGCTGT                    3539
TGGCACTCAC  AGACCTGGAG  CCCCTGGGTG  GGTGGTGGGG  AGGGGCGCTG  GCCCAGCCGG                    3599
```

| | | | | | |
|---|---|---|---|---|---|
| CCTCTCTGGC | CTCCCACCCG | ATGCTGCTTT | CCCCTGTGGG | GATCTCAGGG | GCTGTTTGAG | 3659 |
| GATATATTTT | CACTTTGTGA | TTATTTCACT | TTAGATGCTG | ATGATTTGTT | TTTGTATTTT | 3719 |
| TAATGGGGGT | AGCAGCTGGA | CTACCCACGT | TCTCACACCC | ACCGTCCGCC | CTGCTCCTCC | 3779 |
| CTGGCTGCCC | TGGCCCTGAG | GTGTGGGGGC | TGCAGCATGT | TGCTGAGGAG | TGAGGAATAG | 3839 |
| TTGAGCCCCA | AGTCCTGAAG | AGGCGGGCCA | GCCAGGCGGG | CTCAAGGAAA | GGGGGTCCCA | 3899 |
| GTGGGAGGGG | CAGGCTGACA | TCTGTGTTTC | AAGTGGGGCT | CGCCATGCCG | GGGGTTCATA | 3959 |
| GGTCACTGGC | TCTCCAAGTG | CCAGAGGTGG | GCAGGTGGTG | GCACTGAGCC | CCCCCAACAC | 4019 |
| TGTGCCCTGG | TGGAGAAAGC | ACTGACCTGT | CATGCCCCCC | TCAAACCTCC | TCTTCTGACG | 4079 |
| TGCCTTTTGC | ACCCCTCCCA | TTAGGACAAT | CAGTCCCCTC | CCATCTGGGA | GTCCCCTTTT | 4139 |
| CTTTTCTACC | CTAGCCATTC | CTGGTACCCA | GCCATCTGCC | CAGGGGTGCC | CCCTCCTCTC | 4199 |
| CCATCCCCCT | GCCCTCGTGG | CCAGCCCGGC | TGGTTTTGTA | AGATACTGGG | TTGGTGCACA | 4259 |
| GTGATTTTTT | TCTTGTAATT | TAAACAGGCC | CAGCATTGCT | GGTTCTATTT | AATGGACATG | 4319 |
| AGATAATGTT | AGAGGTTTTA | AAGTGATTAA | ACGTGCAGAC | TATGCAAACC | AAAAAAAAA | 4379 |
| AAAAAAACCG | TCGACAAAGC | GGCCGC | | | | 4405 |

(2) INFORMATION FOR SEQ ID NO:4:

(i) SEQUENCE CHARACTERISTICS:
        (A) LENGTH: 794 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Leu Arg Pro Trp Leu Leu Trp Val Val Ala Ala Thr Gly Thr
 1               5                  10                  15

Leu Val Leu Leu Ala Ala Asp Ala Gln Gly Gln Lys Val Phe Thr Asn
                20                  25                  30

Thr Trp Ala Val Arg Ile Pro Gly Gly Pro Ala Val Ala Asn Ser Val
            35                  40                  45

Ala Arg Lys His Gly Phe Leu Asn Leu Gly Gln Ile Phe Gly Asp Tyr
 50                  55                  60

Tyr His Phe Trp His Arg Gly Val Thr Lys Arg Ser Leu Ser Pro His
65                   70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205
```

-continued

```
Gly Val Cys Gly Val Gly Val Ala Tyr Asn Ala Arg Ile Gly Gly Val
    210             215             220
Arg Met Leu Asp Gly Glu Val Thr Asp Ala Val Glu Ala Arg Ser Leu
225             230             235                         240
Gly Leu Asn Pro Asn His Ile His Ile Tyr Ser Ala Ser Trp Gly Pro
                245             250             255
Glu Asp Asp Gly Lys Thr Val Asp Gly Pro Ala Arg Leu Ala Glu Glu
            260             265             270
Ala Phe Phe Arg Gly Val Ser Gln Gly Arg Gly Gly Leu Gly Ser Ile
        275             280             285
Phe Val Trp Ala Ser Gly Asn Gly Gly Arg Glu His Asp Ser Cys Asn
    290             295             300
Cys Asp Gly Tyr Thr Asn Ser Ile Tyr Thr Leu Ser Ile Ser Ser Ala
305             310             315             320
Thr Gln Phe Gly Asn Val Pro Trp Tyr Ser Glu Ala Cys Ser Ser Thr
            325             330             335
Leu Ala Thr Thr Tyr Ser Ser Gly Asn Gln Asn Glu Lys Gln Ile Val
        340             345             350
Thr Thr Asp Leu Arg Gln Lys Cys Thr Glu Ser His Thr Gly Thr Ser
        355             360             365
Ala Ser Ala Pro Leu Ala Ala Gly Ile Ile Ala Leu Thr Leu Glu Ala
    370             375             380
Asn Lys Asn Leu Thr Trp Arg Asp Met Gln His Leu Val Val Gln Thr
385             390             395             400
Ser Lys Pro Ala His Leu Asn Ala Asn Asp Trp Ala Thr Asn Gly Val
            405             410             415
Gly Arg Lys Val Ser His Ser Tyr Gly Tyr Gly Leu Leu Asp Ala Gly
            420             425             430
Ala Met Val Ala Leu Ala Gln Asn Trp Thr Thr Val Ala Pro Gln Arg
        435             440             445
Lys Cys Ile Ile Asp Ile Leu Thr Glu Pro Lys Asp Ile Gly Lys Arg
    450             455             460
Leu Glu Val Arg Lys Thr Val Thr Ala Cys Leu Gly Glu Pro Asn His
465             470             475             480
Ile Thr Arg Leu Glu His Ala Gln Ala Arg Leu Thr Leu Ser Tyr Asn
            485             490             495
Arg Arg Gly Asp Leu Ala Ile His Leu Val Ser Pro Met Gly Thr Arg
            500             505             510
Ser Thr Leu Leu Ala Ala Arg Pro His Asp Tyr Ser Ala Asp Gly Phe
        515             520             525
Asn Asp Trp Ala Phe Met Thr Thr His Ser Trp Asp Glu Asp Pro Ser
530             535             540
Gly Glu Trp Val Leu Glu Ile Glu Asn Thr Ser Glu Ala Asn Asn Tyr
545             550             555             560
Gly Thr Leu Thr Lys Phe Thr Leu Val Leu Tyr Gly Thr Ala Pro Glu
            565             570             575
Gly Leu Pro Val Pro Pro Glu Ser Ser Gly Cys Lys Thr Leu Thr Ser
            580             585             590
Ser Gln Ala Cys Val Val Cys Glu Glu Gly Phe Ser Leu His Gln Lys
        595             600             605
Ser Cys Val Gln His Cys Pro Pro Gly Phe Ala Pro Gln Val Leu Asp
    610             615             620
```

| | | | | | | | | | | | | | | |
|---|---|---|---|---|---|---|---|---|---|---|---|---|---|---|
| Thr | His | Tyr | Ser | Thr | Glu | Asn | Asp | Val | Glu | Thr | Ile | Arg | Ala | Ser | Val |
| 625 | | | | | 630 | | | | | 635 | | | | | 640 |
| Cys | Ala | Pro | Cys | His | Ala | Ser | Cys | Ala | Thr | Cys | Gln | Gly | Pro | Ala | Leu |
| | | | | 645 | | | | | 650 | | | | | 655 | |
| Thr | Asp | Cys | Leu | Ser | Cys | Pro | Ser | His | Ala | Ser | Leu | Asp | Pro | Val | Glu |
| | | | | 660 | | | | | 665 | | | | | 670 | |
| Gln | Thr | Cys | Ser | Arg | Gln | Ser | Gln | Ser | Ser | Arg | Glu | Ser | Pro | Pro | Gln |
| | | 675 | | | | | 680 | | | | | 685 | | | |
| Gln | Gln | Pro | Pro | Arg | Leu | Pro | Pro | Glu | Val | Glu | Ala | Gly | Gln | Arg | Leu |
| | 690 | | | | | 695 | | | | | 700 | | | | |
| Arg | Ala | Gly | Leu | Leu | Pro | Ser | His | Leu | Pro | Glu | Val | Val | Ala | Gly | Leu |
| 705 | | | | | 710 | | | | | 715 | | | | | 720 |
| Ser | Cys | Ala | Phe | Ile | Val | Leu | Val | Phe | Val | Thr | Val | Phe | Leu | Val | Leu |
| | | | | 725 | | | | | 730 | | | | | 735 | |
| Gln | Leu | Arg | Ser | Gly | Phe | Ser | Phe | Arg | Gly | Val | Lys | Val | Tyr | Thr | Met |
| | | | 740 | | | | | 745 | | | | | 750 | | |
| Asp | Arg | Gly | Leu | Ile | Ser | Tyr | Lys | Gly | Leu | Pro | Pro | Glu | Ala | Trp | Gln |
| | | 755 | | | | | 760 | | | | | 765 | | | |
| Glu | Glu | Cys | Pro | Ser | Asp | Ser | Glu | Glu | Asp | Glu | Gly | Arg | Gly | Glu | Arg |
| | 770 | | | | | 775 | | | | | 780 | | | | |
| Thr | Ala | Phe | Ile | Lys | Asp | Gln | Ser | Ala | Leu | | | | | | |
| 785 | | | | | 790 | | | | | | | | | | |

( 2 ) INFORMATION FOR SEQ ID NO:5:

( i ) SEQUENCE CHARACTERISTICS:
  ( A ) LENGTH: 36 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:5:

CCACCTGTCT GATCAATGGA GCTGAGGCCC TGGTTG     36

( 2 ) INFORMATION FOR SEQ ID NO:6:

( i ) SEQUENCE CHARACTERISTICS:
  ( A ) LENGTH: 36 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:6:

GAGGCCTGAT CACTACTCAG CCAGGTGTGA GGGCAT     36

( 2 ) INFORMATION FOR SEQ ID NO:7:

( i ) SEQUENCE CHARACTERISTICS:
  ( A ) LENGTH: 36 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:7:

GCAGCCTGAT CACTATGGAG GTACGGGCAG CCCCTC     36